(12) United States Patent
Xu

(10) Patent No.: US 8,889,196 B2
(45) Date of Patent: Nov. 18, 2014

(54) DENTAL COMPOSITES COMPRISING NANOPARTICLES OF AMORPHOUS CALCIUM PHOSPHATE

(75) Inventor: Huakun Xu, Frederick, MD (US)

(73) Assignee: University of Maryland, Baltimore, Baltimore, MD (US)

(*) Notice: Subject to any disclaimer, the term of this patent is extended or adjusted under 35 U.S.C. 154(b) by 0 days.

(21) Appl. No.: 13/807,123

(22) PCT Filed: Jun. 30, 2011

(86) PCT No.: PCT/US2011/042550
§ 371 (c)(1),
(2), (4) Date: Dec. 27, 2012

(87) PCT Pub. No.: WO2012/003290
PCT Pub. Date: Jan. 5, 2012

(65) Prior Publication Data
US 2013/0108708 A1    May 2, 2013

Related U.S. Application Data

(60) Provisional application No. 61/360,272, filed on Jun. 30, 2010.

(51) Int. Cl.
| | |
|---|---|
| *A61K 33/38* | (2006.01) |
| *A61K 9/14* | (2006.01) |
| *A61K 47/00* | (2006.01) |
| *A61K 6/033* | (2006.01) |
| *A61K 6/083* | (2006.01) |
| *A61K 6/00* | (2006.01) |
| *A61K 31/22* | (2006.01) |
| *A61K 47/02* | (2006.01) |
| *B82Y 5/00* | (2011.01) |

(52) U.S. Cl.
CPC ............... *A61K 33/38* (2013.01); *A61K 6/033* (2013.01); *A61K 6/083* (2013.01); *A61K 6/0067* (2013.01); *A61K 31/22* (2013.01); *A61K 47/02* (2013.01); *A61K 6/0008* (2013.01); *B82Y 5/00* (2013.01); *Y10S 977/773* (2013.01)
USPC ............ 424/618; 424/489; 514/770; 977/773

(58) Field of Classification Search
CPC ... A61K 6/0008; A61K 6/0067; A61K 6/033; A61K 6/083; A61K 47/02; A61K 31/22; A61K 33/38; C08L 33/10
USPC .................... 424/489, 618; 514/770; 977/773
See application file for complete search history.

(56) References Cited

U.S. PATENT DOCUMENTS

| | | | |
|---|---|---|---|
| 6,461,161 B1 * | 10/2002 | Ngo et al. ............... | 433/217.1 |
| 7,632,878 B2 * | 12/2009 | Xu et al. ................. | 523/116 |
| 8,252,851 B2 * | 8/2012 | Young et al. ............. | 523/116 |
| 2003/0212194 A1 | 11/2003 | Jia | |
| 2005/0038135 A1 | 2/2005 | Jin et al. | |
| 2006/0270752 A1 * | 11/2006 | Xu et al. ................. | 523/116 |
| 2009/0093566 A1 * | 4/2009 | Xu et al. ................. | 523/116 |
| 2009/0208909 A1 * | 8/2009 | Rusin et al. ............. | 433/217.1 |

OTHER PUBLICATIONS

International Search Report for PCT/US2011/042550, dated Mar. 23, 2012.

* cited by examiner

*Primary Examiner* — Blessing M Fubara
(74) *Attorney, Agent, or Firm* — Roylance, Abrams, Berdo & Goodman, L.L.P.

(57) ABSTRACT

Described herein are dental composites comprising amorphous calcium phosphate nanoparticles and methods of making and using the same. The dental composites display increased Ca and $PO_4$ release, improved mechanical properties, and improved antibacterial properties. Anti-bacterial agents, such as quaternary ammonium salts or silver-containing nanoparticles may be included in the composites.

20 Claims, 20 Drawing Sheets

US 8,889,196 B2

DENTAL COMPOSITES COMPRISING NANOPARTICLES OF AMORPHOUS CALCIUM PHOSPHATE

CROSS REFERENCE TO RELATED CASES

This application claims priority to U.S. Provisional Application Ser. No. 61/360,272, filed Jun. 30, 2010, which is herein incorporated by reference in its entirety.

STATEMENT REGARDING FEDERALLY SPONSORED RESEARCH

This invention was made with government support under Grant Number DE017974 awarded by the National Institutes of Health. The government has certain rights in the invention.

BACKGROUND

Tooth caries are the result of a dietary carbohydrate-modified bacterial infectious disease, one of the most common bacterial infections in humans (Loesche, 1986; van Houte, 1994; Featherstone, 2000). The basic mechanism of dental caries is demineralization, or mineral loss, through attack by acid generated by bacteria (Featherstone, 2004; Deng, 2004; Totiam et al., 2007). Therefore, acidogenic bacteria growth and biofilm formation are responsible for dental caries (Loesche, 1986; van Houte, 1994; Zero, 1995; Featherstone, 2000; Deng et al., 2005; Cenci et al., 2009). Plaque formation has been described to have three steps: pellicle formation, bacteria colonization, and biofilm maturation (Burne, 1998). In the initial stage, a proteinaceous film called pellicle forms on the tooth surface with adsorbed components from saliva, mucosa, and bacteria (Carlén et al., 2001). Bacteria then adhere and colonize on this surface to grow into a biofilm, which is a heterogeneous structure consisting of clusters of various types of bacteria embedded in an extracellular matrix (Stoodley et al., 2008). Cariogenic bacteria such as *Streptococcus mutans* (*S. mutans*) and lactobacilli in the plaque can take nutrients from carbohydrates and produce organic acids. Acid production causes demineralization to the tooth structure beneath the biofilm.

Resin composites have been increasingly used for tooth cavity restorations because of their aesthetics, direct-filling capability, and enhanced performance (Ferracane, 1995; Bayne et al., 1998; Lim et al., 2002; Ruddell et al., 2002; Watts et al., 2003; Drummond, 2008). While there has been significant improvement in resin compositions, filler types, and cure conditions since their introduction (Ruddell et al., 2002; Imazato, 2003; Drummond and Bapna, 2003; Watts et al., 2003; Lu et al., 2005; Xu X et al., 2006; Krämer et al., 2006), secondary caries formation and bulk fracture remain challenges to the use of resins (Sarrett, 2005; Sakaguchi, 2005).

Furthermore, resin composites in general do not prevent secondary caries because they do not hinder bacteria colonization and plaque formation. In fact, several studies have indicated that composites have a greater accumulation of bacteria and plaque than other restorative materials (Svanberg et al., 1990; Imazato et al., 1994; Takahashi et al., 2004). Indeed, caries at the restoration margins are a frequent reason for replacing existing restorations (Mjör et al., 2000), accounting for 50-70% of all restorations (Deligeorgi et al., 2001; Frost, 2002). In addition, frequent occurrence of gingivitis was reported when composites were placed at the subgingival area (van Dijken et al., 1991). Replacement dentistry costs $5 billion/year in the U.S. (Jokstad et al., 2001).

Therefore, there is a need for mechanically-strong composites that can inhibit the adherence and growth of bacteria, and thereby prevent secondary caries formation.

SUMMARY

In one embodiment, the present invention is directed to a dental composite comprising nanoparticles of amorphous calcium phosphate (NACP) and a resin, wherein the NACP particles range in size from about 10 nm to about 500 nm, and wherein the NACP comprises about 5% to about 90% of the mass of the composite.

In a second embodiment, the present invention is directed to a dental composite comprising nanoparticles of amorphous calcium phosphate (NACP), a filler and a resin, wherein the NACP particles range in size from about 10 nm to about 500 nm, wherein the NACP comprises about 5% to about 90% of the mass of the composite, and wherein the filler is a glass filler, a ceramic filler or a polymer-based filler. Particular examples of suitable glass fillers include barium boroaluminosilicate, strontium-alumino-fluoro-silicate glass, silicon dioxide, fluoroaluminosilicate glass, a ytterbium tri-fluoride filler, and a fiber glass filler. In certain embodiments, the filler is barium boroaluminosilicate. Particular examples of suitable ceramic fillers include a porcelain filler, a quartz filler, and a zirconia filler.

In each of the embodiments of the invention, the resin is one or more resins selected from the group consisting of bis-GMA (bisphenol glycidyl methacrylate), TEGDMA (triethylene glycol dimethacrylate), HEMA (2-hydroxyethyl methacrylate), UDMA (urethane dimethacrylate), PMGDM (pyromellitic acid glycerol dimethacrylate), ethoxylated bisphenol A dimethacrylate (EBPADMA), methacryloyloxyethyl phthalate (MEP), methacrylate-modified polyalkenoic acid, a hydrophobic monomer, a hydrophilic monomer, a poly acid-modified polymer, a light-cured polymer, a self-cured polymer, a duel cured polymer, and a heat-cured polymer. In certain aspects the resin is a1:1 mass ratio of bis-GMA and TEGDMA.

In each of the embodiments of the invention, the resin may further comprise one or more anti-bacterial agent. Suitable anti-bacterial agents include, but are not limited to, quaternary ammonium salts (QASs), silver-containing nanoparticles (NanoAgs), chlorhexidine particles, $TiO_2$ particles, and ZnO particles.

In certain aspects of each embodiment of the invention, the NACP particles range in size from about 50 nm to about 300 nm, from about 75 nm to about 200 nm, or from about 50 nm to about 200 nm.

In certain aspects of each embodiment of the invention, the NACP comprises about 10% to about 70% of the mass of the composite, about 10% to about 50% of the mass of the composite, about 10% to about 40% of the mass of the composite, or about 10% to about 20% of the mass of the composite.

In a first specific embodiment, the present invention is directed to a dental composite comprising about 10% by mass NACP, about 65% by mass glass filler and about 25% by mass resin, and wherein the NACP particles range in size from about 50 nm to about 200 nm.

In a second specific embodiment, the present invention is directed to a dental composite comprising about 15% by mass NACP, about 60% by mass glass filler and about 25% by mass resin, and wherein the NACP particles range in size from about 50 nm to about 200 nm.

In a third specific embodiment, the present invention is directed to a dental composite comprising about 20% by mass NACP, about 50% by mass glass filler and about 30% by mass resin, and wherein the NACP particles range in size from about 50 nm to about 200 nm.

In a fourth specific embodiment, the present invention is directed to a dental composite comprising about 30% by mass NACP, about 35% by mass glass filler and about 35% by mass resin, and wherein the NACP particles range in size from about 50 nm to about 200 nm.

In a fifth specific embodiment, the present invention is directed to a dental composite comprising about 40% by mass NACP, about 20% by mass glass filler and about 40% by mass resin, and wherein the NACP particles range in size from about 50 nm to about 200 nm.

In certain aspects of each of these specific embodiments, the glass filler is barium boroaluminosilicate, and the resin is a 1:1 mass ratio of bis-GMA and TEGDMA.

In certain aspects of each of these specific embodiments, the resin may further comprise a QAS present in an amount of between about 5% to 70% of the mass fraction of the resin, preferably about 15% to about 50% of the mass fraction of the resin, and NanoAgs present in an amount of between about 0.01% and about 20% of the mass fraction of the resin, preferably 0.08% to 10% of the mass fraction of the resin.

NanoAg, (F) NanoACP+QADM+NanoAg. Live bacteria were stained green, and the compromised bacteria were stained red. When the live and dead bacteria were close to each other or on the top of each other, the green staining was mixed with the red, resulting in yellowish or orange colors. Arrows in D, E and F indicate areas of the compromised bacteria.

Figure 17:
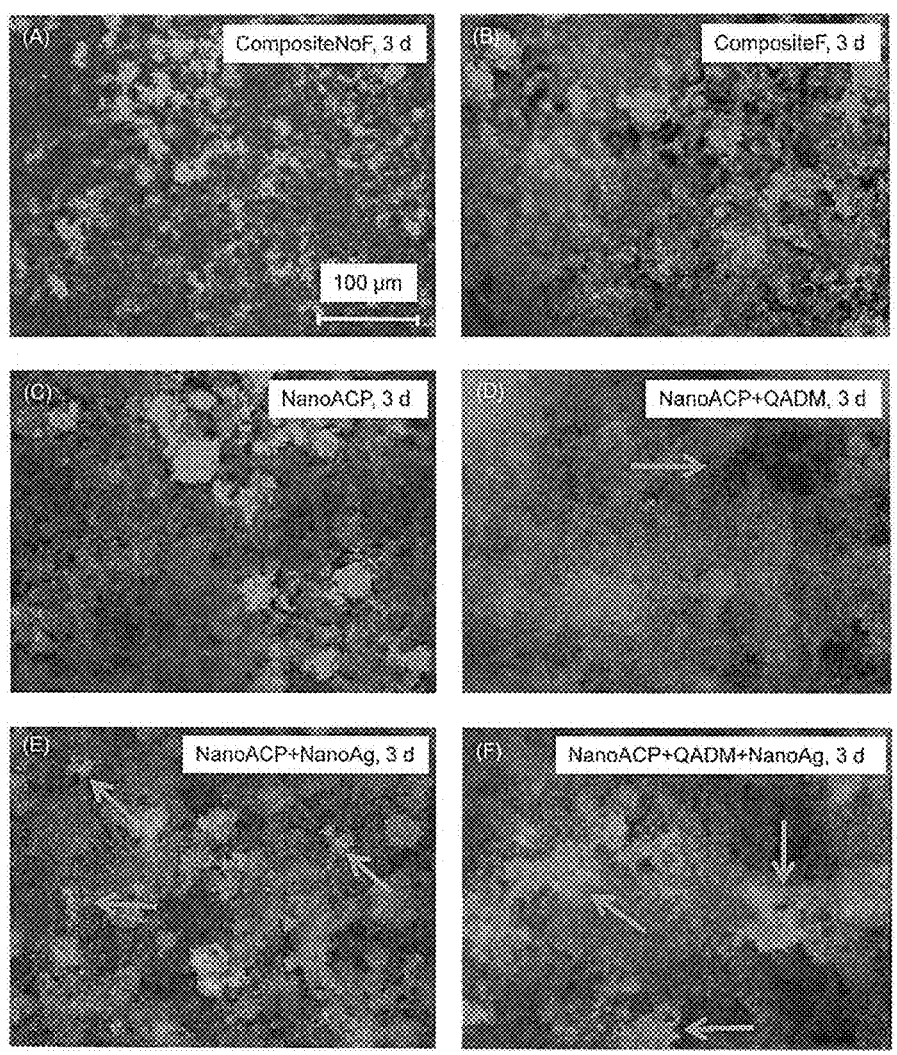

FIG. 17—Live/dead fluorescence images of *S. mutans* biofilms on composites at 3 d on: (A) CompositeNoF, (B) CompositeF, (C) NanoACP, (D) NanoACP+QADM, (E) NanoACP+NanoAg, (F) NanoACP+QADM+NanoAg. Arrows in D, E and F indicate areas of the compromised bacteria. A-C had mature biofilms in which the staining was mostly green, indicating that the bacteria were primarily alive. NanoACP+QADM+NanoAg had the most red/orange staining, indicating the most amounts of compromised bacteria.

Figure 18:
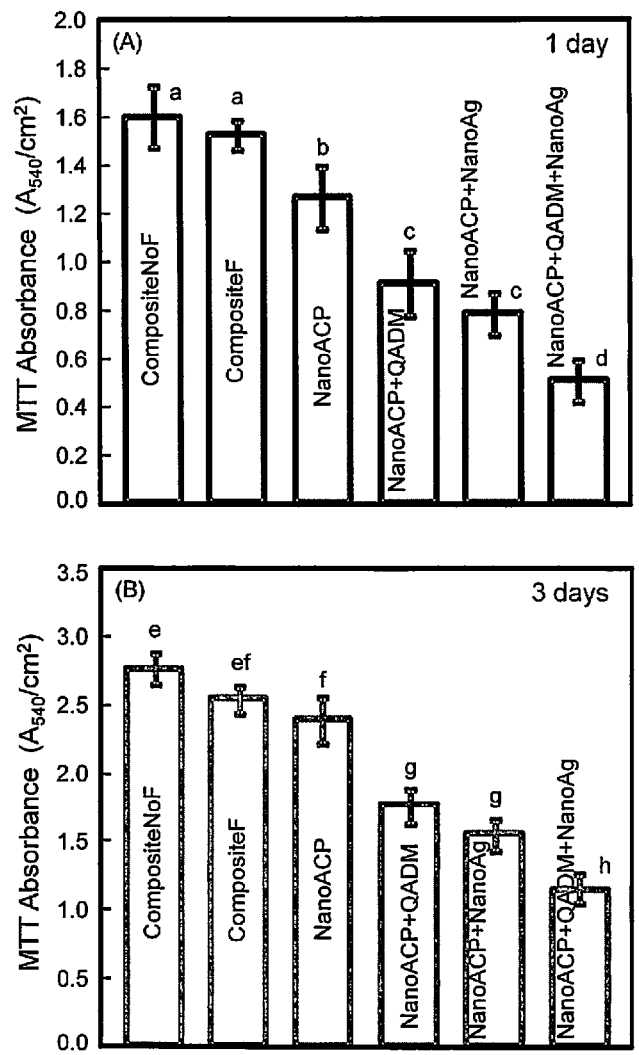

FIG. 18—The metabolic activity of *S. mutans* biofilms adherent on the composite disks was measured via the MTT assay at (A) 1 d, and (B) 3 d. In each plot, values (mean±sd; n=6) with dissimilar letters are significantly different ($p<0.05$).

Figure 19:
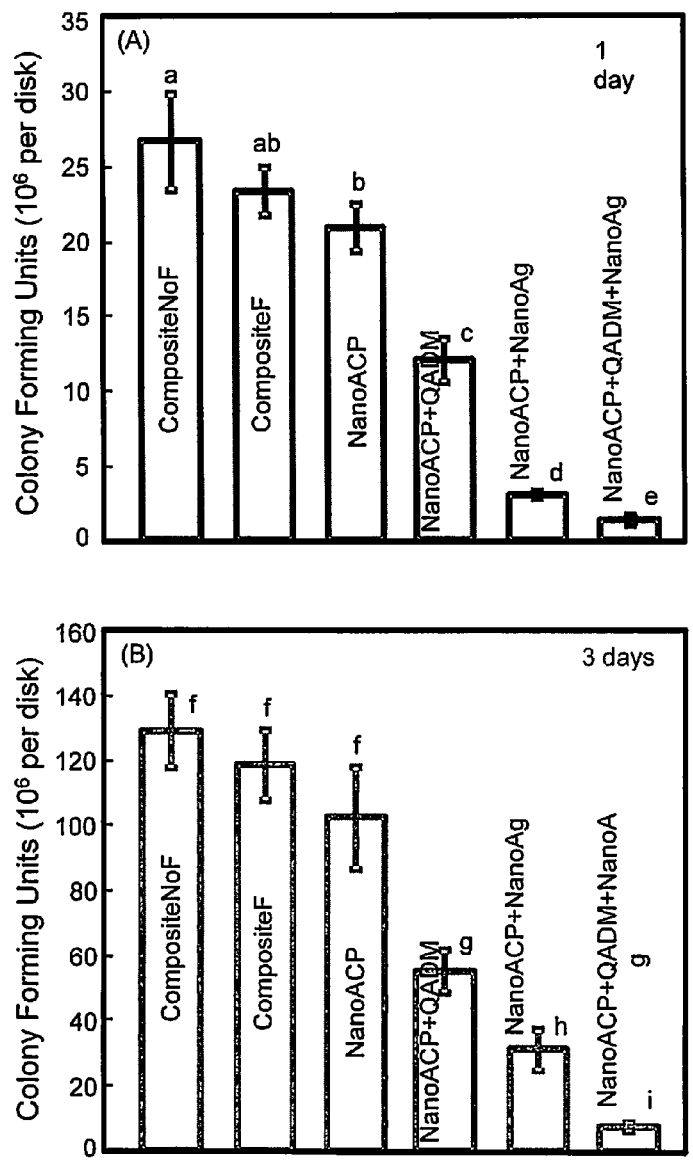

FIG. 19—CFU counts of *S. mutans* biofilms adherent on the composites at (A) 1 d, and (B) 3 d, with the units being $10^6$ bacteria per composite disk. In each plot, the values (mean±sd; n=6) indicated with dissimilar letters are significantly different from each other ($p<0.05$). The NanoACP+QADM+NanoAg composite had the least CFU counts. Its CFU was an order of magnitude less than that of CompositeNoF.

Figure 20:
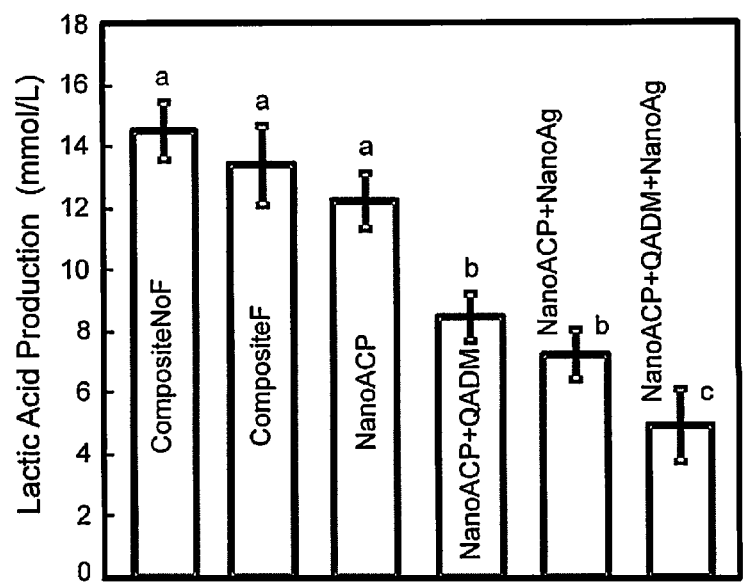

FIG. 20—Lactic acid production by *S. mutans* biofilms adherent on the composite disks. Each value is mean±sd; n=6. Dissimilar letters indicate values that are significantly different from each other ($p<0.05$).

DETAILED DESCRIPTION

Described herein are dental composites comprising nanometer-sized amorphous calcium phosphate ($Ca_3[PO_4]_2$) particles that result in photo-cured nanocomposites with high Ca and $PO_4$ release, improved mechanical properties, and improved antibacterial properties. The composites can be combined with fillers such as aesthetic glass or ceramic fillers. The dental composites allow greatly increased ion release at acidic, cariogenic pH, when these ions are most needed to inhibit caries. The dental composites described herein: (1) are mechanically stronger than a resin-modified glass ionomer; (2) neutralize cariogenic acid and raise the acidic pH to a safe level; and (3) possess antibacterial properties against cariogenic bacteria such as *S. mutans*.

In one embodiment, the present invention is directed to a dental composite comprising nanoparticles of amorphous calcium phosphate (NACP) and a resin, wherein the NACP particles range in size from about 10 nm to about 500 nm, and wherein the NACP comprises about 5% to about 90% of the mass of the composite. The abbreviations "NACP" and "NanoACP" are used interchangeably herein to reference the nanoparticles of amorphous calcium phosphate that comprise the dental composites of the present invention.

In a second embodiment, the present invention is directed to a dental composite comprising nanoparticles of amorphous calcium phosphate (NACP), a filler and a resin, wherein the NACP particles range in size from about 10 nm to about 500 nm, wherein the nanoparticles comprises about 5% to about 90% of the mass of the composite, and wherein the filler is a glass or a ceramic.

The nanoparticles of amorphous calcium phosphate (NACP) used in the dental composites of the present invention will vary in size, but at least about 50, 55, 60, 65, 70, 75, 80, 85, 86, 87, 88, 89, 90, 91, 92, 93, 94, 95, 96, 97, 98 or 99% of the particles, or all of the particles (100%), have an average diameter of between about 10 nm and about 500 nm. In certain aspects, the average diameter will be between about 25 nm and about 400 nm, between about 50 nm and about 300 nm, between about 75 nm and about 200 nm, or between about 100 nm and about 150 nm. In a particular aspect, the NACP particles have an average diameter of between about 50 nm and about 200 nm.

The amount of NACP present in the dental composites of the present invention may vary, but the NACP will generally comprise about 5% to about 90% of the mass of the composite. In certain aspects, the NACP will comprise about 10% to about 70%, about 20% to about 60%, about 20% to about 50%, about 20% to about 40%, about 10% to about 50%, about 10% to about 40%, about 10% to about 30%, or about 10% to about 20% of the mass of the composite. In particular aspects, the NACP will comprise about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 or 45% of the mass of the composite.

The dental composites of the present invention consist of one or more resins in addition to the NACP. The resin may be any resin that is suitable for dental use in a subject, such as a human. Suitable resins will be those resins commonly used in dental applications. Such resins typically comprise a matrix that is of a hardenable dental polymer. Exemplary resins include bis-GMA (bisphenol glycidyl methacrylate), TEGDMA (triethylene glycol dimethacrylate), HEMA (2-hydroxyethyl methacrylate), UDMA (urethane dimethacrylate), PMGDM (pyromellitic acid glycerol dimethacrylate), ethoxylated bisphenol A dimethacrylate (EBPADMA), methacryloyloxyethyl phthalate (MEP), methacrylate-modified polyalkenoic acid, a hydrophobic monomer, a hydrophilic monomer, a poly acid-modified polymer, a light-cured polymer, a self-cured polymer, a duel cured polymer and a heat-cured polymer, as well combinations of two or more of these polymers. A suitable combination is Bis-GMA and TEGDMA at 1:1 mass ratio.

The resins used in the dental composites of the invention may be rendered light-curable through the addition of appropriate compounds to the resin. For example, camphorquinone and ethyl 4-N,N-dimethylaminobenzoate may be added to a resin comprising Bis-GMA and TEGDMA thereby rendering the resin light-curable. In a particular embodiment, about 0.2% camphorquinone and about 0.8% ethyl 4-N,N-dimethylaminobenzoate may be added to a resin comprising Bis-GMA and TEGDMA in about a 1:1 mass ratio to render the resin light-curable.

The resins used in the dental composites of the invention may further comprise one or more anti-bacterial agents. Suitable anti-bacterial agents include, but are not limited to, quaternary ammonium salts (QASs), silver-containing nanoparticles (NanoAgs), chlorhexidine particles, $TiO_2$ particles, and ZnO particles. These anti-bacterial agents may be used alone or in combinations when included in the resin.

Suitable QASs include both polymerizable monomers and non-polymerizable small molecules, and include, but are not limited to, bis(2-methacryloyloxy-ethyl) dimethyl-ammonium bromide (QADM), methacryloyloxydodecylpyridinium bromide, methacryloyloxyethyl benzyl dimethyl ammonium chloride, methacryloyloxyethyl m-chloro benzyl dimethyl ammonium chloride, methacryloyloxyethyl cetyl dimethyl ammonium chloride, cetylpyridinium chloride, and methacryloxylethyl cetyl ammonium chloride, QAS chlorides, QAS bromides, QAS monomethacrylates, QAS dimethacrylates, and pre-fabricated QAS particles.

Suitable silver-containing nanoparticles include, but are not limited to, silver 2-ethylhexanoate salt, silver-containing glass particles and silver benzoate. In addition to silver salts, pre-formed silver nanoparticles can be used.

When present, QAS may make up between about 5% and about 70% of the mass fraction of the resin. In certain aspects, QAS will make up between about 10% and about 60%, between about 15% and about 50%, or between about 20% and about 50% of the mass fraction of the resin, or about 5%, 10%, 15%, 20%, 25%, 30%, 35%, 40%, 45%, 50%, 55%, 60% or 65%, of the mass fraction of the resin. In one embodiment, the resin is BisGMA-TEGDMA in a 1:1 mass ratio comprising QADM in a mass fraction of about 20%.

When present, NanoAg may make up between about 0.01% and about 20% of the mass fraction of the resin. In certain aspects, NanoAg will make up between about 0.05% and about 5%, or 0.08% and about 10%, of the mass fraction of the resin, or about 0.01%, 0.08%, 0.15%, 0.20%, 0.25%, 0.30%, 0.35%, 0.40%, 0.45%, 0.50%, 1.0%, 1.5% or 2.0% of the mass fraction of the resin. In one embodiment, NanoAg makes up about 0.08% of the mass fraction of the resin. The silver particle size can range from about 1 nm to about 1000 nm, and in one aspect, from about 2 nm to about 500 nm. In one embodiment, the resin is BisGMA-TEGDMA in a 1:1 mass ratio comprising NanoAg in a mass fraction of about 0.08%. In another embodiment, the resin is BisGMA-TEGDMA in a 1:1 mass ratio comprising QADM in a mass fraction of about 20% of the resin and NanoAg in a mass fraction of about 0.08% of the resin.

The dental composites of the present invention may optionally contain one or more fillers, in addition to the NACP and the resin. The filler may be used to increase the strength of the composite. Suitable fillers include a glass, a ceramic, and a polymer-based filler. Particular examples of suitable glass fillers include barium boroaluminosilicate, strontium-alumino-fluoro-silicate glass, silicon dioxide, fluoroaluminosilicate glass, a ytterbium tri-fluoride filler, and a fiber glass filler. Particular examples of suitable ceramic fillers include any dental ceramic such as a porcelain filler, a quartz filler, and a zirconia filler. Polymer-based filler includes dental polymer that is pre-polymerized and then ground into filler particles, and polymer fibers.

The size of the particle of the filler will depend on the identity of the filler. As an example, in an embodiment where barium boroaluminosilicate glass particles serve as the filler, the median particle diameter may be between about 0.1 and about 10 µm, or between about 1.0 µm and about 5 µm. Thus, the median particle diameter of the fillers used in the composites of the present invention may, in one aspect where barium boroaluminosilicate glass particles is the filler, be between about 0.1 and about 10 µm, or between about 1.0 µm and about 5 µm. In certain aspects, where barium boroaluminosilicate glass particles is the filler, the median particle diameter may be about 0.6 µm, 0.8 µm, 1.0 µm, 1.2 µm, 1.4 µm, 1.6 µm, 1.8 µm, and 2.0 µm. The skilled artisan will understand that the particle size of the particular filler used will depend on the identity of the filler, and while the sizes provided here are with respect to barium boroaluminosilicate glass particles, similar sizes may pertain to one or more of the alternative fillers described herein.

Depending on the identity of the filler, the particles comprising the filler may be silanized. Suitable means for silanization are known to the skilled artisan and include, but are not limited to, a mixture of about 4% 3-methacryloxypropyltrimethoxysilane and about 2% n-propylamine.

In one embodiment, the filler comprises barium boroaluminosilicate glass particles, where the particles are silanized. In another embodiment, the filler comprises silanized barium boroaluminosilicate glass particles having a median particle diameter of about 1.4 µm.

The amount of filler present in the dental composites of the present invention may vary, but in composites comprising a filler, the filler will generally comprise about 5% to about 90% of the mass of the composite. In certain aspects, the filler will comprise about 10% to about 80%, about 50% to about 80%, about 55% to about 75%, or about 60% to about 70% of the mass of the composite. In particular aspects, the filler will comprise about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80% of the mass of the composite.

In particular examples of the present invention, the dental composite comprises:
(i) about 10% NACP, about 65% glass filler and about 25% resin, or
(ii) about 15% NACP, about 60% glass filler and about 25% resin, or
(iii) about 20% NACP, about 50% glass filler and about 30% resin, or
(iv) about 30% NACP, about 35% glass filler and about 35% resin, or
(v) about 40% NACP, about 20% glass filler and about 40% resin, or
(vi) about 30% NACP, about 35% barium boroaluminosilicate glass and about 35% BisGMA-TEGDMA-QADM (20% QADM of the mass fraction of the resin), or
(vii) about 30% NACP, about 35% barium boroaluminosilicate glass and about 35% BisGMA-TEGDMA-NanoAg (0.08% NanoAg of the mass fraction of the resin), or
(viii) about 30% NACP, about 35% barium boroaluminosilicate glass and about 35% BisGMA-TEGDMA-QADM-NanoAg (20% QADM of the mass fraction of the resin; 0.08% NanoAg of the mass fraction of the resin).

In aspects of examples (i)-(v), the glass filler is barium boroaluminosilicate, and in each of the examples, the resin may be a 1:1 mass ratio of bis-GMA and TEGDMA.

The dental composites of the present invention are suitable for use in the teeth of mammals, including primates such as human or non-human primates, and those of dogs, cats, horses, cattle, pigs, goats and sheep, for example.

The dental composites described herein can be used in a method of inhibiting growth of aciduric bacteria on a surface of a tooth of a subject, comprising restoring a surface of the tooth from which a decayed portion has been removed by administering a dental composite as described herein to the surface of the tooth, thereby inhibiting growth of aciduric bacteria on the tooth of the subject.

The dental composites described herein can also be used in a method of inhibiting further decay of a decaying tooth in a subject, comprising restoring a surface of the tooth from which a decayed portion has been removed by administering a dental composite as described herein to the surface of the tooth, thereby inhibiting further decay of the decaying tooth in the subject.

EXAMPLES

Example 1

Synthesis of ACP Nanoparticles

A spray-drying technique was used to make nanoparticles of ACP. ACP is important because it is a precursor that can convert to apatite, similar to the minerals in tooth enamel and dentin. A spraying solution was prepared by adding 1.5125 g of acetic acid glacial (J. T. Baker, Phillipsburg, N.J.) into 500 mL of distilled water. Then, 0.8 g of calcium carbonate ($CaCO_3$, Fisher, Fair Lawn, N.J.) and 5.094 g of DCPA (Baker) were dissolved into the acetic acid solution. This solution was then added with distilled water to a total of 1 liter. The final Ca and $PO_4$ ionic concentrations were 8 mmol/L and 5.333 mmol/L, respectively. This yields a Ca/P molar ratio of 1.5, the same as that for ACP. The acetic acid concentration was 25 mmol/L. This solution was sprayed at a feed rate of 10 mL/min, through a nozzle (PNR, Poughkeepsie, N.Y.) that was situated on the top of a heated glass column. An electrostatic precipitator (AirQuality, Minneapolis, Minn.) was connected to the lower end of the column and drew air from the column to create a steady flow of air/mist. The water/volatile acid were evaporated into the dry, heated column and expelled from the precipitator into an exhaust-hood. The dried particles were collected by the electrostatic precipitator.

The collected powder was examined with X-ray diffractometry (XRD, DMAX2200, Rigaku, Woodlands, Tex.). The specific surface area of the powder was analyzed using a multipoint-BET (Brunauer, Emmet, and Teller) method (AU-TOSORB-1, Quantachrome, Boynton Beach, Fla.) and transmission electron microscopy (TEM, 3010-HREM, JEOL, Peabody, Mass.).

Nanocomposite Fabrication

Barium boroaluminosilicate glass particles of a median diameter of 1.4 µm (Caulk/Dentsply, Milford, Del.) were used as a filler, selected because it is a typical dental glass filler similar to those in a hybrid composite (TPH, Cault/Dentsply). The glass particles were silanized with 4% 3-methacryloxypropyltrimethoxysilane and 2% n-propylamine (mass %). A resin of Bis-GMA (bisphenol glycidyl dimethacrylate) and TEGDMA (triethylene glycol dimethacrylate) at 1:1 mass ratio was rendered light-curable with 0.2% camphorquinone and 0.8% ethyl 4-N,N-dimethylaminobenzoate which made up the remaining mass of the composites.

The glass fillers are designated as "glass", and the nano-sized ACP particles are designated as "NACP". Four composites were made with the following fillers: (1) 0% NACP+75% glass; (2) 10% NACP+65% glass; (3) 15% NACP+60% glass; and (4) 20% NACP+50% glass. The total filler mass fraction was 75% except for (4) which had 70%. This was because with 20% NACP, the paste was relatively dry at 75% total filler level. NACP filler levels higher than 20% were not used in order for the NACP composite to have mechanical properties matching/exceeding a commercial control composite. The fillers and resin were mixed, and the paste was placed into a stainless steel mold of 2×2×25 mm. The specimen was photo-cured (Triad 2000, Dentsply, York, Pa.) for 1 min on each side. The specimens were then incubated at 37° C. for 24 h prior to testing.

Two commercial materials were used as comparative controls. A composite with nano-fillers (40-200 nm) and a low level of fluoride release served as a control (Heliomolar, Ivoclar, Ontario, Canada). The fillers consisted of silica and ytterbium-trifluoride (total filler mass fraction=66.7%). Heliomolar is indicated for Class I and Class II restorations in the posterior region, Class III and Class IV anterior restorations, Class V restorations, and pit and fissure sealing in molar and premolar teeth. A resin-modified glass ionomer (Vitremer, 3M, St. Paul, Minn.), another control, consisted of fluoroaluminosilicate glass, and a light-sensitive, aqueous polyalkenoic acid. Indications include Class III, V and root-caries restoration, Class I and II in primary teeth, and core-buildup. A powder/liquid ratio of 2.5/1 was used (filler mass fraction=71.4%) according to the manufacturer. Both materials were photo-cured.

Flexural Testing

Flexural strength and elastic modulus were measured using a three-point flexural test with a 20-mm span at a crosshead-speed of 1 mm/min on a computer-controlled Universal Testing Machine (5500R, MTS, Cary, N.C.) (Xu et al., 2008). Flexural strength was calculated by: $S=3P_{max}L/(2bh^2)$, where $P_{max}$ is the fracture load, L is span, b is specimen width and h is thickness. Elastic modulus was calculated by: $E=(P/d)(L^3/[4bh^3])$, where load P divided by displacement d is the slope of the load-displacement curve in the linear elastic region.

Ca and $PO_4$ Ion Release

A sodium chloride (NaCl) solution (133 mmol/L) was buffered to three different pHs: pH 4 with 50 mmol/L lactic acid, pH 5.5 with 50 mmol/L acetic acid, and pH 7 with 50 mmol/L HEPES. Following previous studies (Xu et al., 2006, 2007a), three specimens of approximately 2×2×12 mm were immersed in 50 mL of solution at each pH, yielding a specimen volume/solution of 2.9 $mm^3$/mL. This compared to a specimen volume per solution of approximately 3.0 $mm^3$/mL in a previous study (Skrtic et al., 1996). For each solution, the concentrations of Ca and $PO_4$ released from the specimens were measured at 1, 3, 7, 14, 21, and 28 days (d). At each time, aliquots of 0.5 mL were removed and replaced by fresh solution. The aliquots were analyzed for Ca and $PO_4$ via a spectrophotometric method (DMS-80 UV-visible, Varian, Palo Alto, Calif.) using known standards and calibration curves (Skrtic et al., 1996; Dickens et al., 2003).

One-way and two-way ANOVA were performed to detect the significant effects of the variables. Tukey's multiple comparison test was used to compare the data at a p value of 0.05.

Results

Figure 1:
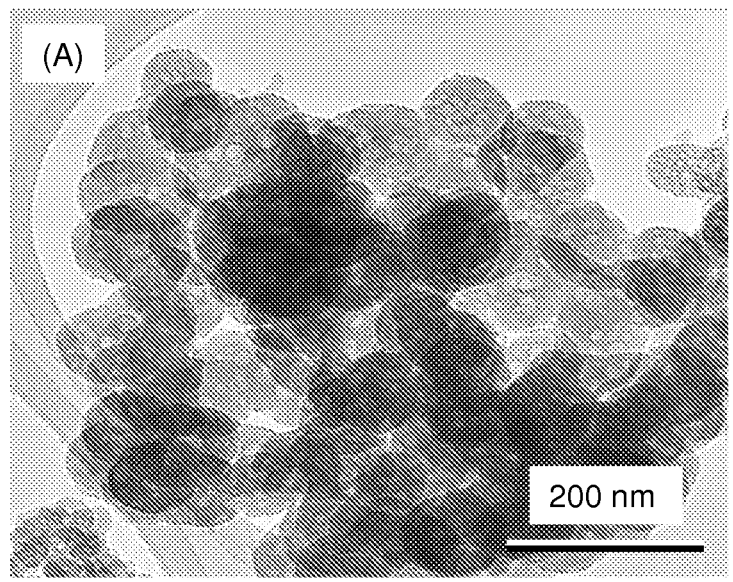
FIG. 1—NACP synthesized via a spray-drying technique (NACP refers to nano-sized amorphous calcium phosphate particles). (A) A typical TEM micrograph of the NACP particles. (B) The X-ray diffraction (XRD) pattern shows that the spray-dried powder was amorphous.
Figure 1:
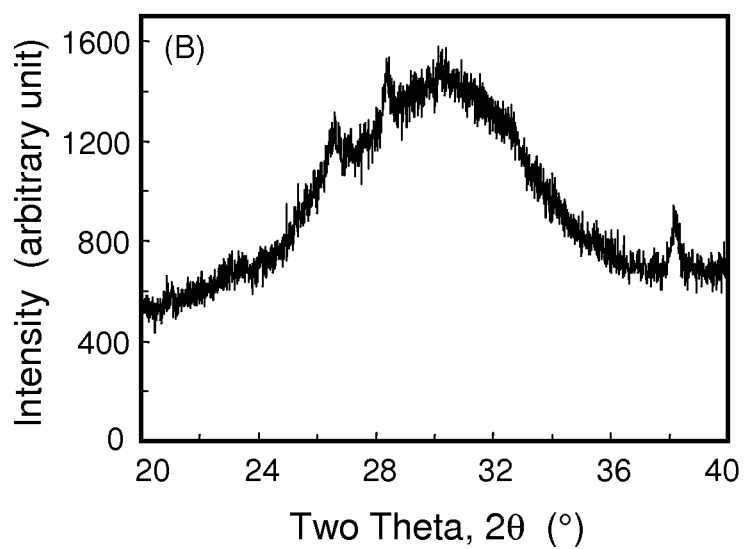

FIG. 1 shows the spray-dried NACP powder. In (A), the NACP particles appeared to have sizes of about 100 nm. Some agglomerations are visible. The particles appeared to have smaller particles inside and had numerous spherical protuberances on the surfaces, suggesting that they were formed during the spray-drying process through the fusion of much smaller particles. The XRD pattern in (B) showed that the powder was amorphous. The BET method yielded a NACP surface area A=17.76 $m^2$/g. With ACP density ρ=2.9 g/$cm^3$, the particle diameter d=6/(A ρ)=116 nm.

Figure 2:
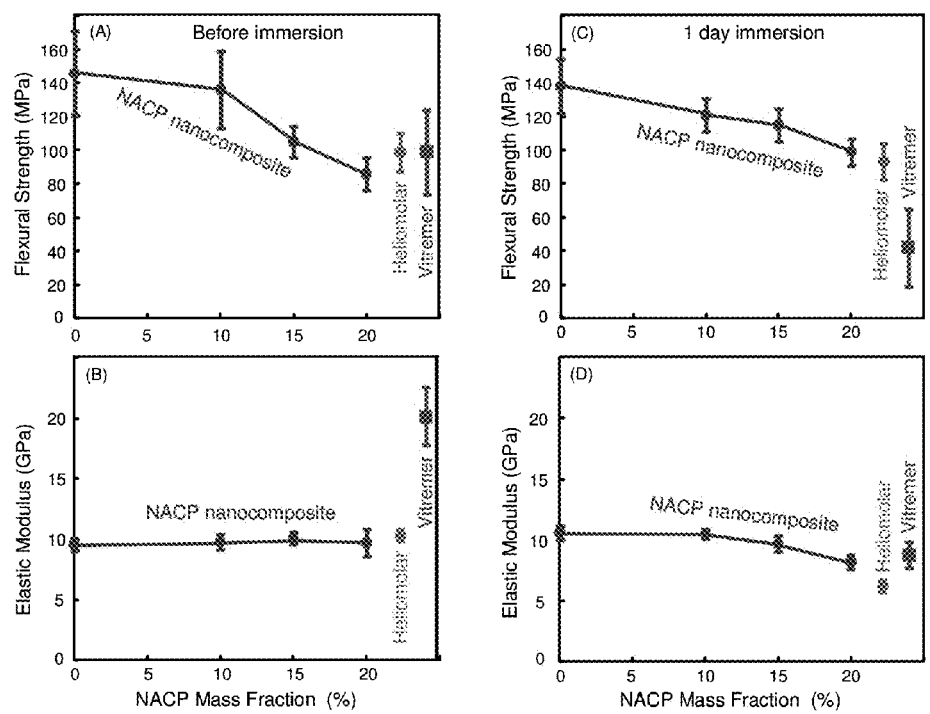
FIG. 2—Mechanical properties of NACP composites. (A) Flexural strength before immersion. (B) Elastic modulus before immersion. (C) Flexural strength after 1 d immersion. (B) Elastic modulus after 1 d immersion. The properties for the NACP composites are plotted vs. NACP filler level. The two commercial materials are near the right axis as controls. Each value is the mean of six measurement, with the error bar showing one standard deviation (mean±sd; n=6).

The composite mechanical properties are plotted in FIG. 2: (A and B) Before immersion, and (C and D) after 1 d immersion. In (A), the strength (mean±sd; n=6) at 0% and 10% NACP were significantly higher than that at 20% NACP ($p<0.05$). The strengths of the two commercial materials were not significantly different from any of the NACP composites ($p>0.1$). Vitremer had a significantly ($p<0.05$) higher elastic modulus than the other materials (B). After 1 d immersion (C), the strength of each material was not significantly lower than that before immersion, except for Vitremer which showed a precipitous decrease ($p<0.05$).

Figure 3:
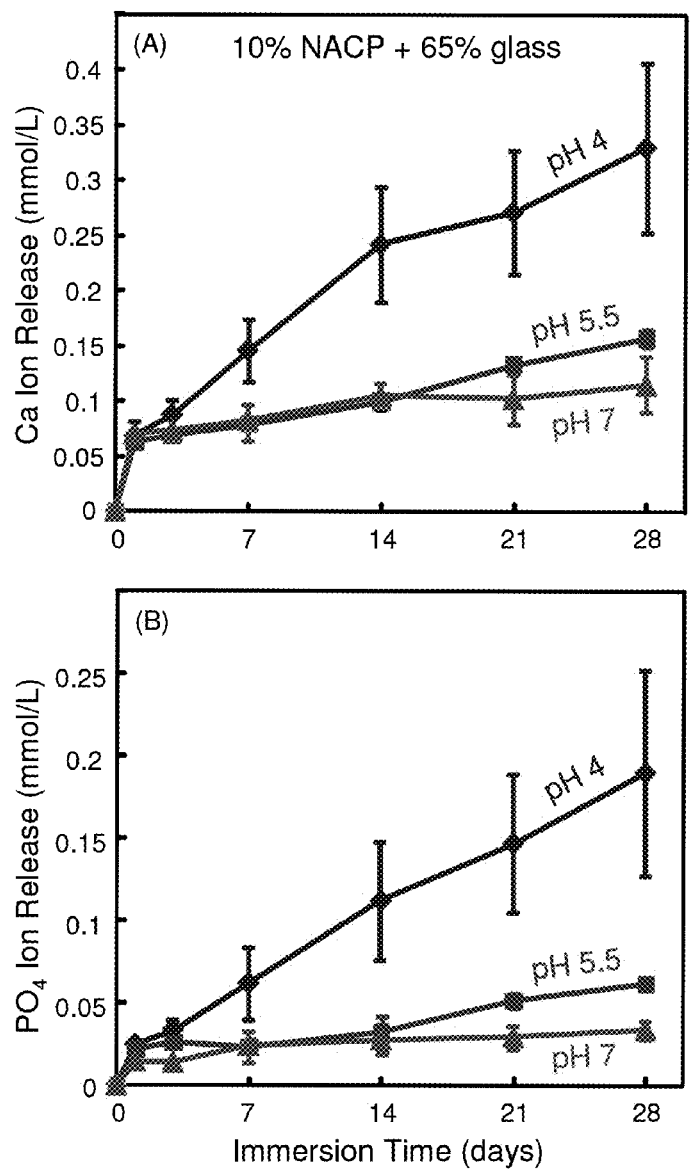
FIG. 3—Ca and $PO_4$ ion release from the composite filled with 10% NACP and 65% glass. (A) Ca and (B) $PO_4$ release continuously increased with increasing the immersion time. Ca and $PO_4$ release increased with decreasing the solution pH (mean±sd; n=3).
Figure 4:
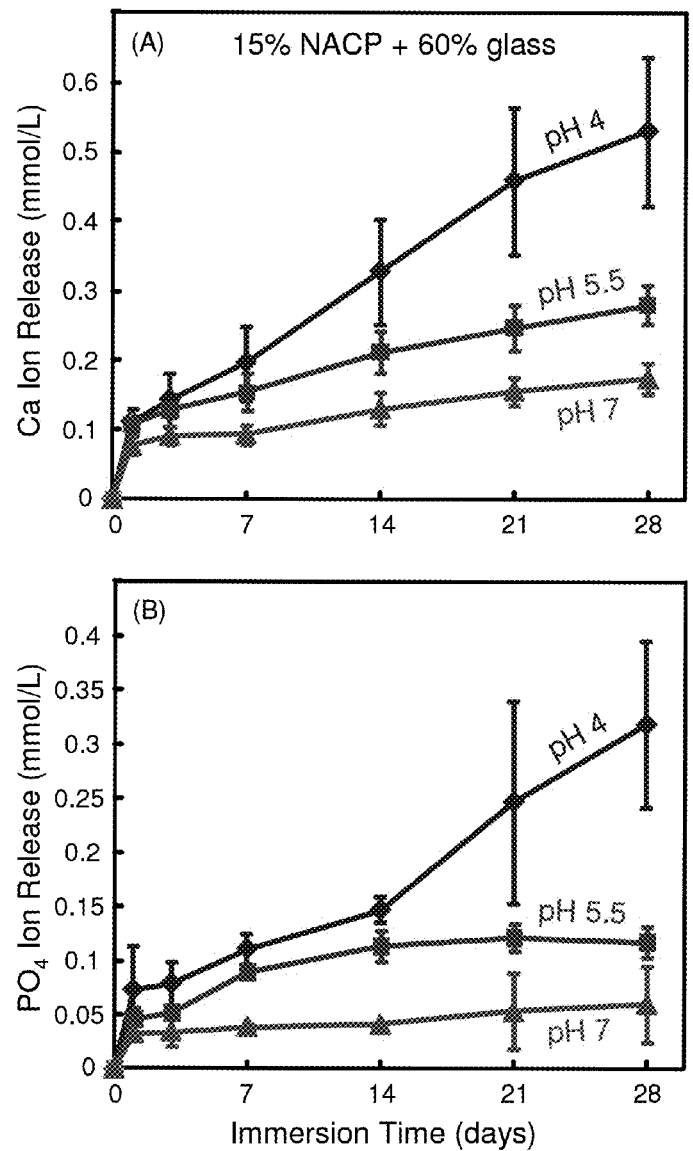
FIG. 4—Ca and $PO_4$ ion release from the composite containing 15% NACP and 60% glass. The (A) Ca and (B) $PO_4$ release continuously increased with increasing the immersion time, and increased with decreasing the solution pH (mean±sd; n=3).
Figure 5:
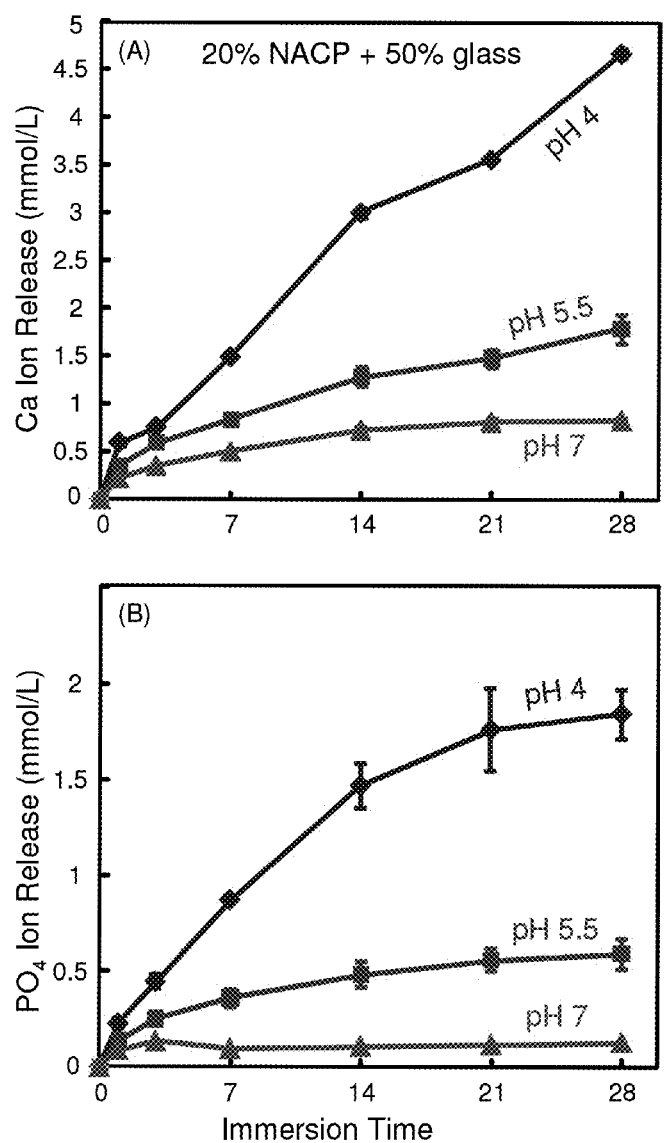
FIG. 5—Ca and $PO_4$ ion release from the composite with 20% NACP and 50% glass. (A) Ca and (B) $PO_4$ release continuously increased with increasing the immersion time, and increased with decreasing the solution pH (mean±sd; n=3). Compared with the release at 10% and 15% NACP, increasing the NACP filler level to 20% significantly increased the ion release ($p<0.05$).

Ca and $PO_4$ release are plotted in FIGS. 3, 4 and 5, at 10%, 15% and 20% NACP, respectively. Decreasing the solution pH significantly increased the ion release. At 20% NACP, for example, the $PO_4$ release at 28 d was (1.84±0.12) mmol/L at pH 4, significantly higher than (0.59±0.08) at pH 5.5, and (0.12±0.01) at pH 7 ($p<0.05$).

Furthermore, increasing the NACP filler level increased the ion release. For example, at 28 d and pH 4, the Ca release was (4.66±0.05) mmol/L at 20% NACP, much higher than (0.53=0.11) at 15% NACP, and (0.33±0.08) at 10% NACP ($p<0.05$).

Figure 6:
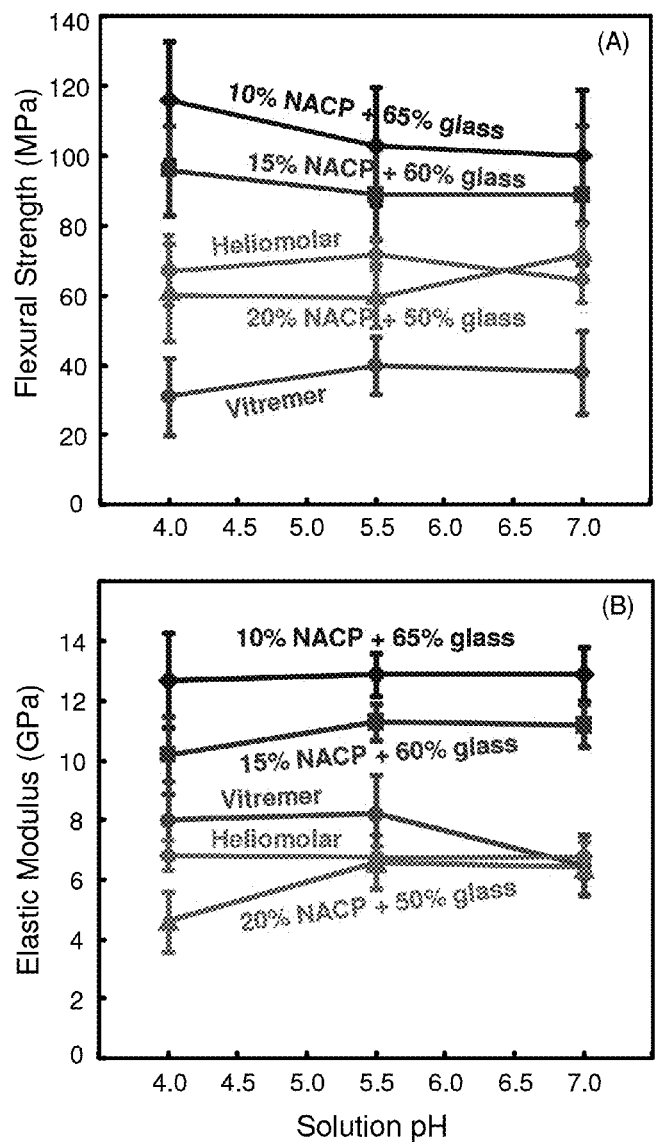
FIG. 6—Mechanical properties of NACP composites after immersion for 28 d in solutions at different pH. (A) Flexural strength. (B) Elastic modulus. For every material, varying the solution pH from 4 to 7 did not significantly change the strength or modulus ($p>0.1$).

The composite mechanical properties after immersion for 28 d at different pH are shown in FIG. 6. In (A), for every material, varying the pH from 4 to 7 did not significantly change the strength (p>0.1). For example, the flexural strength at 15% NACP was (96±13) MPa at pH 4, similar to (89±13) MPa at pH 5.5, and (89±19) MPa at pH 7 (p>0.1). Between different materials, composites with 10% and 15% NACP had the highest strengths. Heliomolar and nanocomposite with 20% NACP had similar strengths, and Vitremer had slightly lower strengths.

Discussion

A major advantage of the dental composite comprising NACP of the present invention is that because of the high surface area of the nanoparticles, high levels of Ca and $PO_4$ release was achieved at relatively low NACP filler levels. Furthermore, dental composite with 20% NACP allowed for a significant amount of reinforcing glass fillers. The dental composite thus relied on the stable glass fillers, not the releasing CaP fillers, for mechanical strength. As a result, the dental composite with high levels of ion release possessed mechanical properties matching/exceeding those of a commercial composite with little ion release (Heliomolar).

The dental composite of the present study had flexural strengths of 60-120 MPa after immersion in solution of pH 4, 5.5 and 7 for 28 d.

The dental composite had mechanical properties that matched/exceeded those of a commercial composite with little ion release (Heliomolar). Since Heliomolar is indicated for Class I and II posterior restorations, Class III and IV anterior restorations and Class V restorations, the dental composites of the invention can similarly be used for these applications, with an important additional benefit of high release of Ca and $PO_4$ to inhibit caries. Hence, combining NACP with glass yielded dental composites with a combination of Ca and $PO_4$ release and stress-bearing properties, which may help reduce secondary-caries and restoration fracture.

Figure 7:
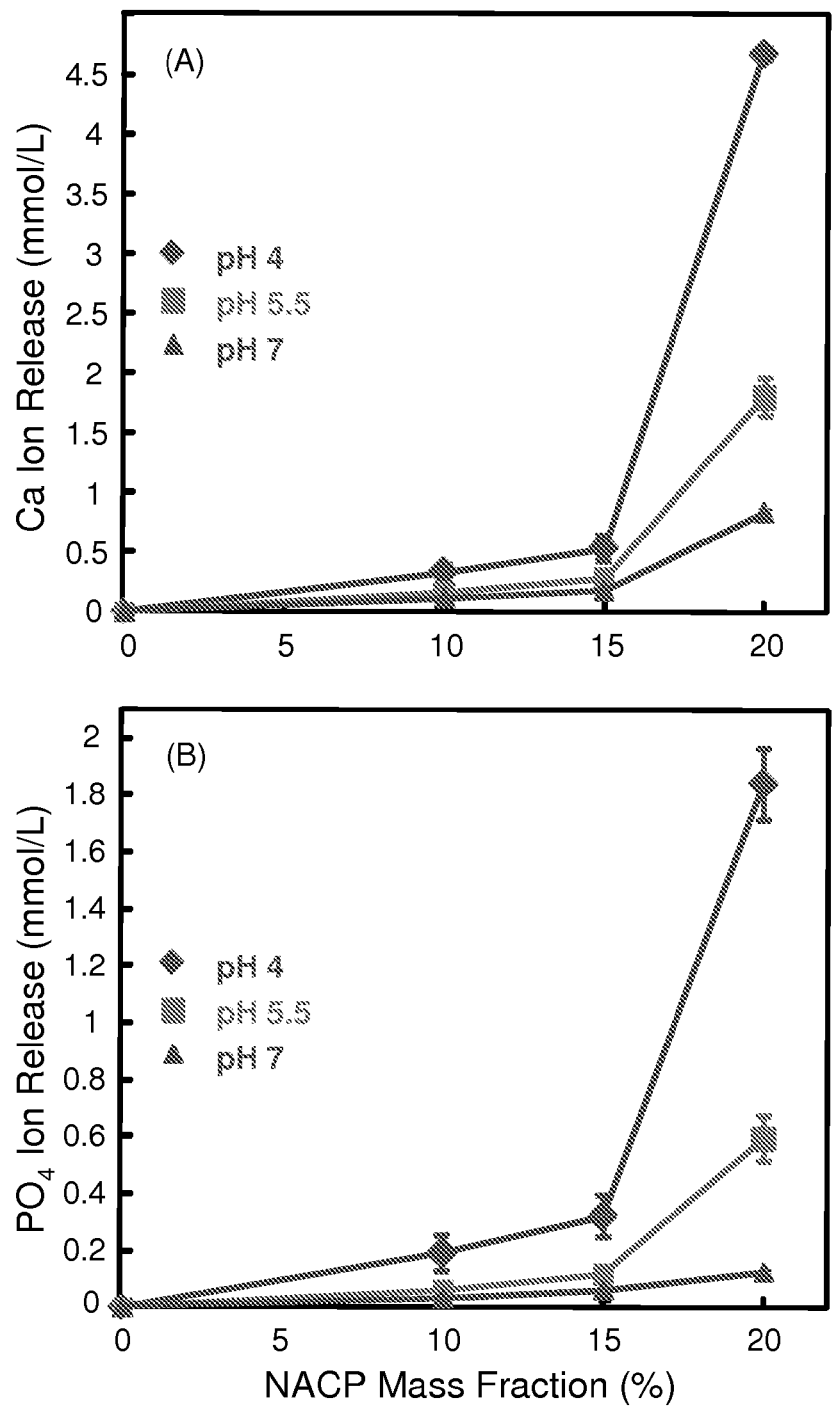
FIG. 7—Effect of NACP filler level on ion release from the composites. (A) Ca and (B) $PO_4$ concentrations (mean±sd; n=3) at 28 d are plotted vs. NACP filler level. At each pH, the Ca and $PO_4$ release increased rapidly with increasing the NACP content in the composite.

The effects of NACP level on ion release, as shown by Ca and $PO_4$ concentrations at 28 d, are plotted in FIG. 7. It shows that when the NACP content was increased from 10% to 15%, there was a moderate increase in ion release. However, further increase to 20% NACP resulted in dramatically higher ion releases. The Ca and $PO_4$ release increased with NACP level at a rate faster than being linear. This is consistent with the relationship between ion release and dicalcium phosphate anhydrous level in dicalcium phosphate anhydrous nanocomposites (Xu et al., 2007a). While not wishing to be bound by theory, it is speculated that increasing the level of NACP in the dental composites not only increases the source of ions for release, but also increases the number of interfaces in the dental composite. The interfacial surface areas between the NACP particles and the dental composite provide passageways for water to diffuse in, and ions to diffuse out. In addition, increasing the NACP surface area moderately decreases the polymerization conversion, likely due to a higher concentration of air on the filler surfaces which decreased the conversion (Xu et al., 2007b). As a result, when the NACP level is increased, there is not only more source for ion release, there is also enhanced diffusion of water and ions through the composite due to more interfacial areas and lower polymerization conversion. Therefore, the Ca and $PO_4$ release increases with increasing NACP content at a rate faster than being linear.

Another key factor is the effect of pH. In the oral cavity, a local plaque pH of above 6 is the safe zone, pH of 6.0-5.5 is potentially cariogenic, and pH of 5.5-4 is the cariogenic or danger zone (Hefferren and Koehler, 1981). The present Example shows that the new NACP nancomposites are "smart" and greatly increase the Ca and $PO_4$ release when the pH is reduced from neutral to a cariogenic pH of 4. There was a 5-10 fold increase in ion release when the pH was lowered from 7 to 4, when these ions are most needed for caries inhibition. The immersion for 28 d in solutions of pH 7, 5.5, and 4 reduced the mechanical properties of the composites, compared to those before immersion. However, as long as the specimens were immersed, pH variation from 4 to 7 did not have a significant effect on the mechanical properties. For every material tested, the flexural strength and elastic modulus at the three different pHs were not significantly different. Therefore, the increase in the Ca and $PO_4$ release at cariogenic pH is achieved without compromising the mechanical properties of the composites, relative to the mechanical properties of the composites at neutral pH.

The NACP dental composites can be used in a range of tooth cavity restorations. For example, they can be used in load-bearing restorations for which the current CaP composites and resin-modified glass ionomer restoratives are inadequate. The NACP dental composites can also be used in treatments where complete removal of caries tissue is contraindicated, in teeth where carious lesions are beginning to occur, and for patients at high risk for dental caries including those receiving radiation treatments or with dry mouth. In addition, the NACP dental composites can be used in combination with fluoride-releasing dentifrices and mouthrinses, which can enhance the caries-inhibition and remineralization efficacy via the formation of fluoroapatite with increased resistance to acid attacks.

Example 2

Spray-Drying ACP Nanoparticles

In the present study, nanoparticles of ACP ($Ca_3[PO_4]_2$) were synthesized using a spray-drying technique and incorporated into a dental composite to develop acid-neutralizing and antimicrobial composite.

The spray-drying apparatus has been described previously (Chow et al., 2004; Xu et al., 2006). To make nanoparticles of ACP, referred to as NACP, a solution was prepared by adding 1.5125 g of acetic acid glacial (J. T. Baker, Phillipsburg, N.J.) into 500 mL of distilled water. Then, 0.8 g of calcium carbonate ($CaCO_3$, Fisher, Fair Lawn, N.J.) and 5.094 g of DCPA (Baker) were dissolved into the acetic acid solution. This solution was added with distilled water to a total of 1 liter. The final Ca and $PO_4$ ionic concentrations were 8 mmol/L and 5.333 mmol/L, respectively. This yields a Ca/P molar ratio of 1.5, the same as that for ACP. This solution was sprayed into a heated glass column to be dried. An electrostatic precipitator (AirQuality, Minneapolis, Minn.) was connected to the lower end of the column to collect the dried particles. A separate study showed that the collected NACP particles had a size of 116 nm (Xu et al., 2010).

Resin Composite Fabrication

Four mass fractions of NACP were used: 10%, 20%, 30%, and 40%. As a filler, barium boroaluminosilicate glass particles of a median diameter of 1.4 μm (Caulk/Dentsply, Milford, Del.) were silanized with 4% 3-methacryloxypropyltrimethoxysilane and 2% n-propylamine (Xu et al., 2007b). A resin of Bis-GMA (bisphenol glycidyl dimethacrylate) and TEGDMA (triethylene glycol dimethacrylate) at 1:1 mass ratio was rendered light-curable with 0.2% camphorquinone and 0.8% ethyl 4-N,N-dimethylaminobenzoate which made up the remaining mass of the composites.

Four nanocomposites were made: (1) 10% NACP+65% glass; (2) 20% NACP+50% glass; (3) 30% NACP+35% glass;

and (4) 40% NACP+20% glass. The total glass filler level was gradually reduced when the NACP amount was increased to maintain a similar working viscosity for the paste by the same operator. This was because nanoparticles with a higher surface area required more resin to form a cohesive paste. The paste was placed into a mold of 2×2×25 mm. Specimens were photo-cured (Triad 2000, Dentsply, York, Pa.) for 1 min on each side.

A commercial composite (TPH, Caulk/Dentsply, Milford, Del.) was used as a control and referred to as "hybrid composite". It consisted of barium glass and fumed silica with a mean size of about 0.8 µm, at 78% filler level by mass in a urethane-modified Bis-GMA-TEGDMA resin. It is clinically used in anterior and posterior restorations. A resin-modified glass ionomer (referred to as "RMGI") (Vitremer, 3M, St. Paul, Minn.) served as a second control. It consisted of fluoroaluminosilicate glass and a light-sensitive, aqueous polyalkenoic acid. Indications for Vitremer include Class III, V and root-caries restoration, Class I and II in primary teeth, and core-buildup. A powder/liquid ratio of 2.5/1 was used according to the manufacturer. As a third control, a microfill composite with nano-fillers (40-200 nm) and a low level of fluoride release (Heliomolar, Ivoclar, Ontario, Canada) was used (referred to as "microfill composite"). The Heliomolar fillers consisted of silica and ytterbium-trifluoride (total filler mass fraction=66.7%). Heliomolar is indicated for Class I and Class II posterior restorations, Class III and Class IV anterior restorations, and Class V restorations. All materials were photo-cured (Triad-2000) for 1 min on each side, and then incubated at 37° C. for 24 h.

Flexural Testing

The bar specimens were immersed in distilled water at 37° C. for 1 day, and then fractured in three-point flexure with a 20-mm span at a crosshead-speed of 1 mm/min on a computer-controlled Universal Testing Machine (5500R, MTS, Cary, N.C.). Flexural strength was calculated by: $S=3P_{max}L/(2bh^2)$, where $P_{max}$ is the fracture load, L is span, b is specimen width and h is thickness. Elastic modulus was calculated by: $E=(P/d)(L^3/[4bh^3])$, where load P divided by displacement d is the slope of the load-displacement curve.

Acid Neutralization

To characterize the acid neutralization ability of the composites, a sodium chloride (NaCl) solution (133 mmol/L) was buffered to pH 4 with 5 mmol/L lactic acid. Three specimens of 2×2×12 mm were immersed in each vial, following previous studies (Xu et al., 2006, 2009). One mL of the pH 4 solution was used to submerge the three bars, yielding a composite volume/acid volume ratio of 0.14/1. Acid solution of 1 mL was used because in reality in vivo, the volume of the bacteria-produced acid on the composite restoration of the tooth cavity would not be larger than the volume of the restoration. Hence, acid solution of more than 1 mL was not used because it would render the composite volume being too small compared to the acid volume. Acid solution of less than 1 mL was not used because the 1 mL solution was needed to amply submerge the composite specimens. As soon as the specimens were submerged in the acid solution, the pH of the solution was monitored with a combination pH electrode (Orion, Cambridge, Mass.). The pH was recorded versus time which was continued for 90 minutes. In addition, the acid neutralization capacity of the composite was calculated using software (Chemist, Micromath Research, St. Louis, Mo.). The calculation used a simulation in which potassium hydroxide (KOH), a typical base, was added to the 1 mL solution of pH 4 to raise the pH. The amount of potassium hydroxide that would need to be added, in order to raise the pH to the measured pH, was used to represent the acid neutralization capacity of the composite.

Antibacterial Measurement

S. mutans bacteria were used because they were a major species of bacteria that produces organic acids responsible for dental caries (Loesche, 1986; Featherstone, 2004). S. mutans was obtained from American Type Culture Collection (ATCC 700610, Manassas, Va.). The use of S. mutans was approved by the University of Maryland (IBC-00000794). S. mutans was cultured at 37° C. with the infusion of 5% supplemented $CO_2$ in a Brain Heart Infusion broth (BHI, Difco, Detroit, Mich.) from stock culture and used for the experiments.

Three materials were tested in the agar disk-diffusion test: Nanocomposite with 40% NACP and 20% glass; hybrid composite (TPH); and RMGI (Vitremer). Disks were fabricated in molds of 9 mm diameter and 2 mm thickness and photo-cured. The disks were sterilized in an ethylene oxide sterilizer (Andersen, Haw River, N.C.) for 1 d and degassed for 3 d. The sterilized disk was placed onto a BHI agar plate inoculated with 350 µL of 1×10⁸ CFU/mL of S. mutans suspension (Imazato et al., 1994), and the plate was incubated at 37° C. for 48 h. In the agar disk-diffusion test, the release of antibacterial agents from the disk would kill the bacteria around the disk. This would create a ring of inhibition zone around the disk. A composite without the release of antibacterial agent would have no inhibition zone (Imazato, 2003).

To examine bacterial growth on the bottom surface of the disk, the disk was removed from the agar plate. The bottom surface of the disk was examined via the method of crystal violet staining (Sigma, St. Louis, Mo.), in which the S. mutans adhering on the specimen stained a purple color (Imazato, 1994; Hostacka et al., 2010). Photographs were taken of stained specimens with a camera (Nikon Digital Sight, Nikon, Melville, N.Y.) attached to a microscope (Nikon Eclipse TE 2000-S). To quantify the area of the disk that was covered by bacteria, a NIS-Elements BR software (Nikon) was used to estimate the percentage of area that was covered by the bacteria (=the area stained purple/the total surface area of the disk).

Disk specimens were placed in a BHI agar plate inoculated with 350 µL of 1×10⁸ CFU/mL of S. mutans suspension. After incubation for 48 h, the disks were removed and prepared for examination with scanning electron microscopy (SEM). The specimen was rinsed with phosphate buffered saline (PBS), and then immersed in 1% glutaraldehyde in PBS for 4 h at 4° C. The specimens were rinsed with PBS and subjected to graded ethanol dehydrations. They were then rinsed twice with 100% hexamethyldisilazane (Xu and Simon, 2005). The specimens were then sputter-coated with gold and examined via SEM (JEOL 5300, Peabody, Mass.).

One-way and two-way ANOVA were performed to detect the significant effects of the variables. Tukey's multiple comparison test was used at a p value of 0.05 to compare the data.

Results

Figure 8:
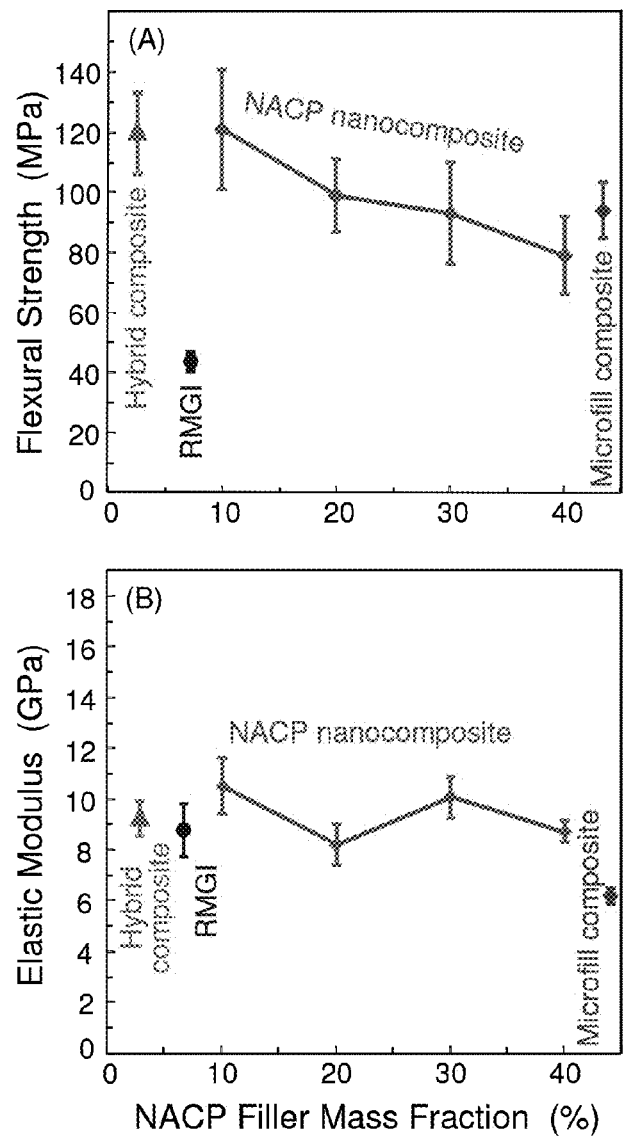
FIG. 8—Mechanical properties: (A) flexural strength, and (B) elastic modulus of NACP composites, microfill composite, hybrid composite, and RMGI. Each value is the mean of five measurements, with the error bar showing one standard deviation (mean±sd; n=5). The composite at 40% NACP had a strength not significantly different from that of the microfill composite ($p>0.1$).

FIG. 8 plots (A) flexural strength, and (B) elastic modulus of the NACP composites with different NACP mass fractions, along with the microfill composite, hybrid composite and RMGI. The composite strength at 10% to 30% NACP matched the strength of microfill composite and hybrid composite (p>0.1). Increasing the NACP level, while decreasing the glass filler level, significantly decreased the strength (p<0.05). The composite at 40% NACP had a strength of (79±5) MPa, significantly (p<0.05) lower than (121±10) MPa at 10% NACP, and (120±13) MPa of the hybrid composite. However, the composite strength at 40% NACP was not significantly different from the (93±10) MPa of the microfill composite (p>0.1). All these composites had strengths that were 2-3 fold that of the RMGI. The elastic moduli were generally similar between the different materials ($p>0.1$), except the microfill composite which had a lower modulus ($p<0.05$).

Figure 9:
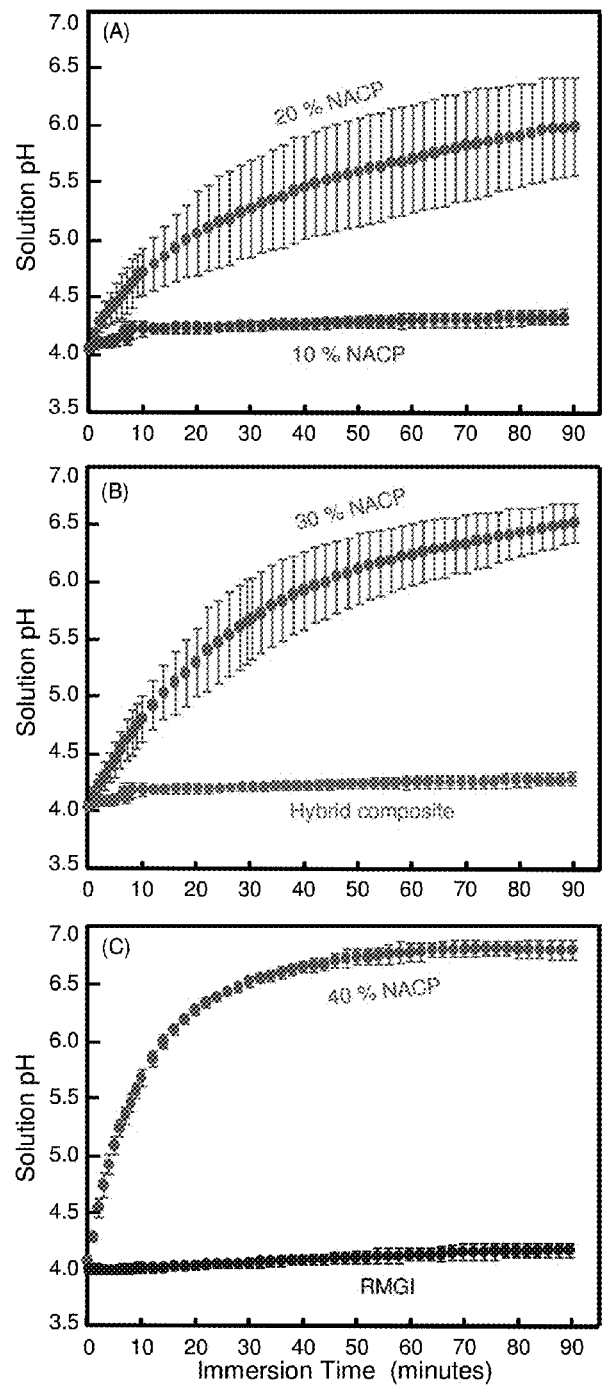
FIG. 9—Increasing the pH of a cariogenic solution. (A) Composite containing 10% and 20% NACP, (B) composite with 30% NACP, and hybrid composite, (C) composite with 40% NACP, and RMGI. The data for the microfill composite were similar to those of the hybrid composite and RMGI, and were not included for clarity. Each datum is mean±sd; n=4. NACP composite neutralized the acid and increased the pH.

The acid neutralization results are plotted in FIG. 9 for: (A) composite with 10% and 20% NACP, (B) composite with 30% NACP, and hybrid composite, (C) composite with 40% NACP, and RMGI. The pH curve for the hybrid composite, RMGI and microfill composite (not shown) were similar to each other, with little increase in pH. In contrast, the composite with 20%-40% NACP greatly increased the pH. Therefore, the NACP composite had a strong ability to neutralize the acid and increase the pH.

Figure 10:
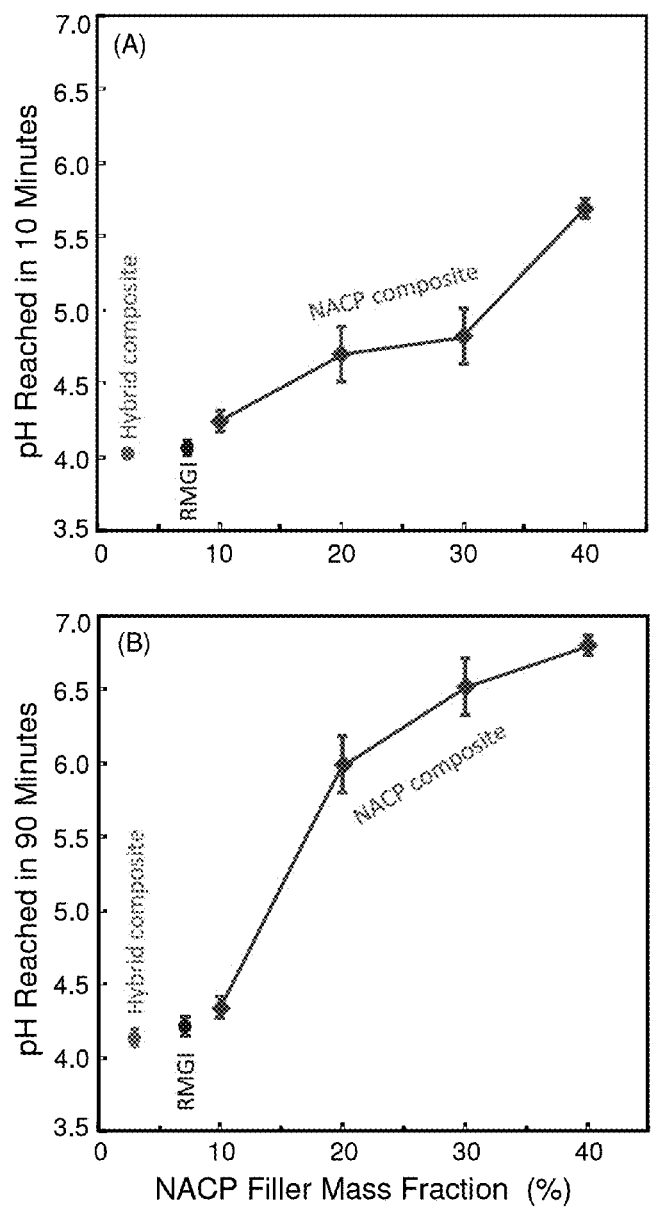
FIG. 10—pH increase vs. NACP filler level. (A) The pH reached at 10 min, and (B) the pH reached at 90 min (mean±sd; n=4). The pH was significantly higher with higher NACP filler level. The pH values were much higher for the composites with 20% or more NACP fillers, compared to the commercial restoratives.

FIG. 10 plots (A) the solution pH reached at 10 min, and (B) the pH reached at 90 min. At 10 min after the specimens were immersed in the pH 4 solution, the pH became 5.69±0.07 for composite with 40% NACP, higher than all other materials ($p<0.05$). RMGI reached a pH of 4.06±0.03. The hybrid composite reached a pH of 4.05±0.02. At 90 min, the solution containing the composite with 40% NACP reached a pH of 6.80±0.08, much higher than 4.21±0.05 for RMGI, and 4.14±0.03 for hybrid composite ($p<0.05$).

Figure 11:
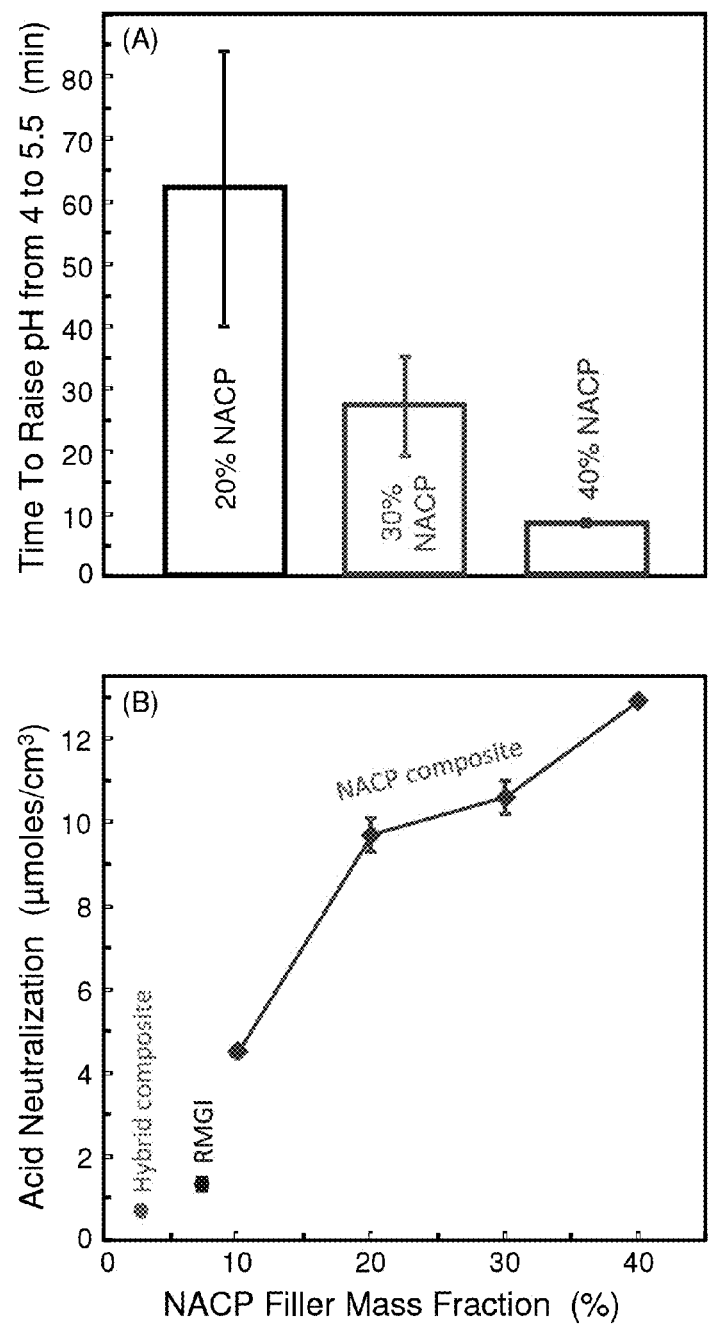
FIG. 11—Acid neutralization. (A) The time it took for the composite to increase the solution pH from a cariogenic pH of 4 to a critical pH of 5.5, above which it is relatively safe for the tooth structure. (B) Acid neutralization capacity. It was evaluated by calculating the amount of a base (potassium hydroxide) that would need to be added to the pH 4 solution, in order to increase the pH to the measured value. The µmoles of base was normalized by the composite volume to yield the acid neutralization capacity, with units of $\mu moles/(cm)^3$ (mean±sd; n=4).

Because it is desirable for the composite to quickly raise the pH from a cariogenic pH to the critical pH of 5.5, FIG. 11A plots the time it took for the composite to increase the solution pH from 4 to 5.5. It took the composite with 40% NACP (8.2±0.5) min to reach pH 5.5, much faster than (27±8) min for the 30% NACP composite, and (62±22) min for the 20% NACP composite ($p<0.05$). In comparison, the solutions containing RMGI, microfill and hybrid composites never reached a pH of 5.5.

The acid neutralization capacity was evaluated by calculating the amount of a base (potassium hydroxide) that would need to be added to the pH 4 solution, in order to increase the pH to the measured value. In FIG. 11B, the measured pH at 10 min was used to calculate the μmoles of potassium hydroxide that would be needed to reach the same pH. The composite volume in the 1 mL solution was 0.144 (cm)$^3$. The calculated μmoles of base was normalized by the composite volume to yield the acid neutralization capacity. The acid neutralization capacity was (12.9±0.1) μmoles/cm$^3$ for the composite with 40% NACP, higher than those of all other materials ($p<0.05$). This value was 10-fold the (1.3±0.1) μmoles/cm$^3$ for RMGI.

Figure 12:
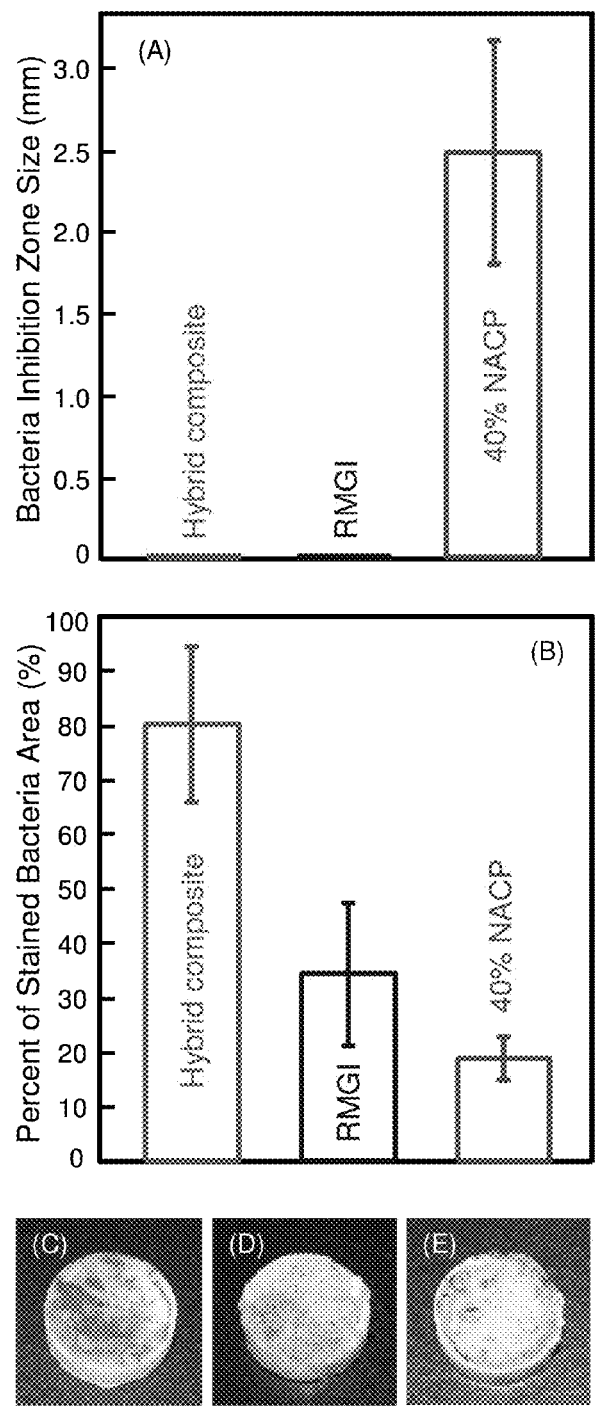
FIG. 12—Antibacterial properties. (A) Bacteria inhibition zone size from the agar disk-diffusion test. (B) Percentage of stained bacteria area on the bottom surface of the disk. (C) More bacteria staining on hybrid composite, (D) intermediate staining on RMGI, and (E) minimal staining on the composite with 40% NACP. In (A), the hybrid composite and RMGI showed no zone of bacteria inhibition, while the inhibition zone was (2.5±0.7) mm for the composite with 40% NACP (mean±sd; n=3).

FIG. 12 shows the results on antibacterial properties of the materials: (A) Bacteria inhibition zone size, and (B) percentage of stained bacterial area on the disk. The photos in (C-E) showed that the hybrid composite had the most purple staining, RMGI had the medium staining, and the composite with 40% NACP had the least staining.

Figure 13:
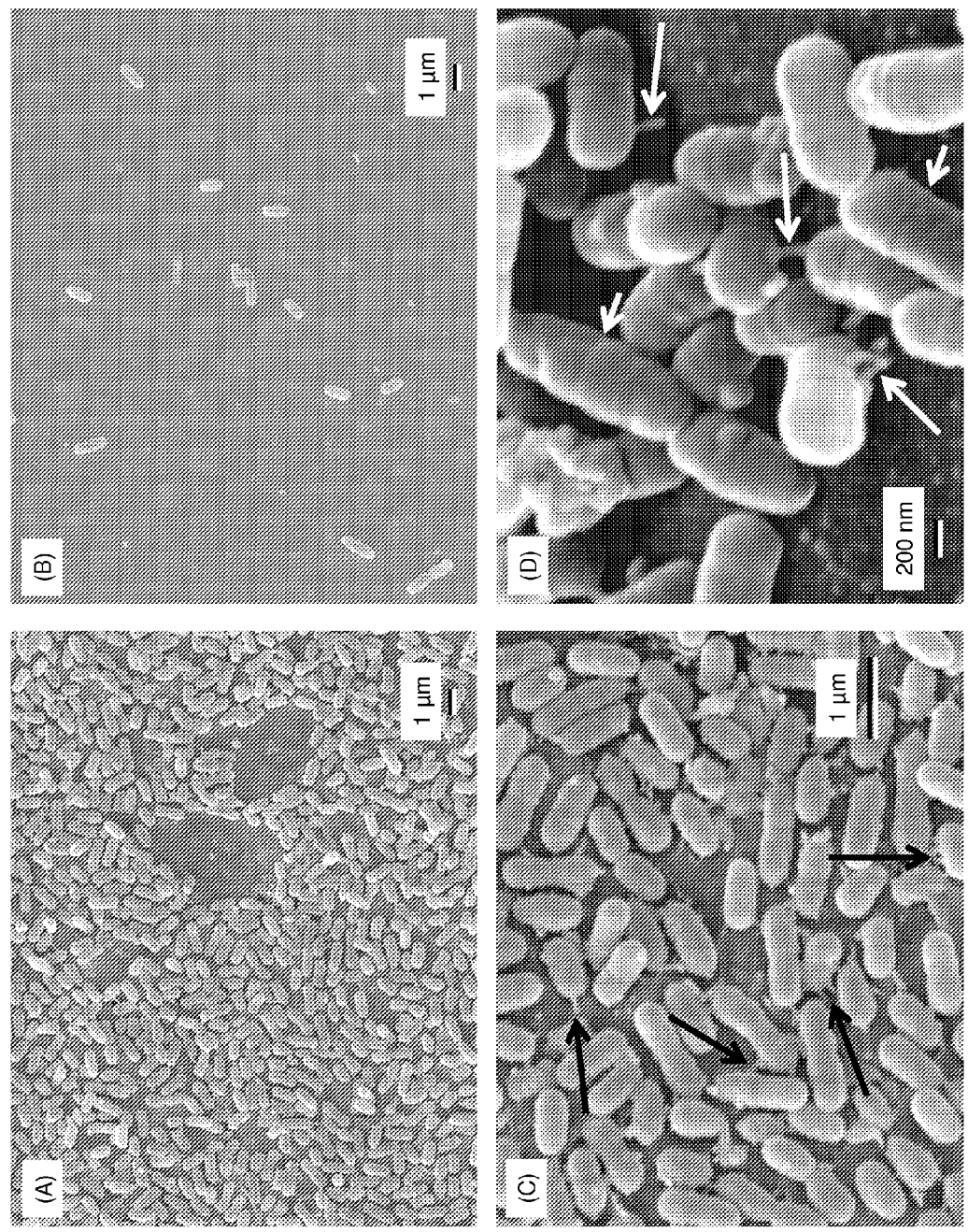
FIG. 13—SEM micrographs of *S. mutans* on: (A) Hybrid composite, (B) composite with 40% NACP, (C) hybrid composite at an intermediate magnification, and (D) hybrid composite at a high magnification. The hybrid composite was nearly entirely covered by bacteria. The RMGI (not shown) had less bacteria coverage. The composite (B) had the least bacteria. The bacterial cells had developed extensions (indicated by arrows in C). These extensions are shown more clearly in (D) as indicated by the long arrows. *S. mutans* had the shape of a short rod with wall bands on its surface (indicated by the short arrows).

FIG. 13 shows SEM micrographs of *S. mutans* adherence on: (A) Hybrid composite, (B) composite with 40% NACP, and (C) and (D) hybrid composite at higher magnification. The hybrid composite surface had numerous bacteria. The NACP composite had minimal bacterial adherence. The bacterial cells had developed extensions (arrows in C) that appeared to form junctions between neighboring bacteria as well as adhering to the composite surface. These extensions are shown more clearly in (D) as indicated by the long arrows. In addition, the *S. mutans* cell body had the shape of a short rod with wail hands on its surface (short arrows).

Discussion

In the present study, novel NACP composites were developed with two strategies to inhibit caries. The first strategy was to neutralize the acids that otherwise would be dissolving the tooth structure. Acidogenic bacteria ferment carbohydrates and produce organic acids including lactic, formic, acetic and propionic acids (Featherstone, 2004). As a result, the oral plaque pH after a sucrose rinse can decrease to 4.5 or even 4 (Hefferren et al., 1981; Thylstrup et al., 1986). There appears to be a critical pH, below which demineralization dominates, leading to a net tooth mineral dissolution (Dawes, 2003). This critical pH varies with ionic concentrations of the oral fluid, but is approximately 5.5 for most individuals (Dawes, 2003). The Stephan Curve shows that the plaque pH, following a glucose mouthrinse, stays in the cariogenic area for about 30 min, and then increases back to a safe pH of 5.5 or higher, after the bacteria have completed their metabolization of the glucose and the saliva has buffered the acid (Hefferren et al., 1981). Hence, the damage is done within the first 30 min after a glucose rinse. Therefore, it would be highly desirable for the composite restoration to quickly neutralize the local acids and raise the cariogenic pH from 4 to a safe pH of 5.5 or above, thereby to help inhibit caries.

The present study demonstrated that when a commercial hybrid composite, a microfill composite, and a resin-modified glass ionomer were immersed in a lactic acid solution of pH 4, they all failed to raise the pH to the critical pH of 5.5. In fact, the pH stayed at near 4. In contrast, the NACP composite was able to rapidly increase the pH. The ability of acid neutralization greatly increased with higher NACP filler levels. This was manifested by the much higher solution pH that was reached at 10 minutes as well as at 90 minutes, and by a much shorter time it took for the solution to reach the critical pH of 5.5. It should be noted that the composite volume was much smaller than the acid volume in this in vitro study. The composite restoration volume in vivo in the tooth cavity is usually larger than the acid volume produced by the bacteria on the restoration. A larger composite with a smaller amount of acid is expected to result in an even faster acid neutralization speed and a higher pH. This pilot study showed that NACP composites have a unique and highly desirable acid neutralization feature which the commercial restoratives do not have. Hence the NACP composite is promising as a new type of restoration to protect tooth structure and inhibit caries.

Besides neutralizing the bacterial acids, another strategy to inhibit caries is to develop antibacterial composites, which directly eradicates the cause of bacterial acids and hence caries. Resin composites typically show no inhibitory effect against plaque formation. The NACP composites of the present study possessed acid neutralization capacity (FIGS. 9-11), antibacterial properties (FIGS. 12, 13), and calcium and phosphate ion release (Xu et al., 2010). The *S. mutans* attachment on the surface of the composite with 40% NACP was reduced to be ½ that of a resin-modified glass ionomer, and ¼ that of a hybrid composite. Besides inhibiting bacterial attachment, another potential benefit of a composite that can raise the local pH is the modification of the microenvironment of the dental plaque. The presence of organic acids in the plaque can result in an increase in the proportion of acidogenic bacteria which have a high acid tolerance (aciduric), at the expense of the other benign bacteria that are less acid-tolerant (Loesche, 1986; Burne, 1998). The normal plaque contains less than 1% of acidogenic bacteria in the oral flora (Featherstone, 2004). The repeated acidification in the plaque with an increasingly more acidic milieu results in the predominance of acidogenic and aciduric bacteria such as *S. mutans* that can preferentially survive well (van Houte, 1994). Therefore, a composite that can raise the local pH can help the survival of the benign bacteria and maintain a normal oral flora, which can exert a protective effect on the tooth by preventing the dominance of cariogenic bacteria.

The SEM observation in FIG. 13 confirmed the measurement of stained bacteria area in FIG. 12. The hybrid composite surface was nearly entirely covered by *S. mutans* cells, consistent with previous studies showing that composites readily had bacteria accumulation (Svanberg et al., 1990; Imazato et al., 1994; Takahashi et al., 2004). The much reduced bacteria adherence in FIG. 13B on the composite with 40% NACP agrees with the bacteria inhibition data in FIG. 12. The S. mutans showed a rod shape with wall bands on the surface (FIG. 13D). A coccus (plural cocci) is any bacterium that has a spheroidal shape. A *diplococcus* consists of two cocci connected by a wall band. S. mutans is formed by the linkage of diplococci and, hence, has a rod shape with wall bands on its surface (Lee et al., 2006). The S. mutans shape and wall band features in FIG. 13 are consistent with previous observations (Lee et al., 2006). The number of wall bands suggested that these S. mutans cells each consisted of 2-3 diplococci.

The two main challenges facing dental composite restorations are secondary caries and bulk fracture. Therefore, besides antibacterial properties, there is also a need for the composite to have load-bearing properties. The photo-cured composites with 10-30% NACP matched the strength of a hybrid composite for posterior and anterior restorations. The composite at 40% NACP had a strength that was not significantly different from a microfill composite (Heliomolar). Since Heliomolar is indicated for Class I and II posterior restorations and Class III and IV anterior restorations, the new NACP composites can similarly be used for these applications, with two important benefits of acid neutralization and antibacterial properties. All the NACP composites had strengths much higher than that of the resin-modified glass ionomer.

Example 3

Fabrication of NACP Nanocomposite

A spray-drying technique as described previously (Chow et al., 2004; Xu H et al., 2006) was used to make nanoparticles of ACP ($Ca_3[PO_4]_2$), which are referred to as NanoACP. Briefly, calcium carbonate ($CaCO_3$, Fisher, Fair Lawn, N.J.) and dicalcium phosphate anhydrous ($CaHPO_4$, Baker Chemical Co., Phillipsburg, N.J.) were dissolved into an acetic acid solution to obtain final Ca and $PO_4$ ionic concentrations of 8 mmol/L and 5.333 mmol/L, respectively. This resulted in a Ca/P molar ratio of 1.5, the same as that for ACP. This solution was sprayed into a heated spray-drying chamber to be dried, and an electrostatic precipitator (AirQuality, Minneapolis, Minn.) was used to collect the dried particles. This method produced NanoACP with a mean particle size of 116 nm, as measured in a previous study (Xu et al., 2011).

As a co-filler for mechanical reinforcement, barium boroaluminosilicate glass particles of a median diameter of 1.4 µm (Caulk/Dentsply, Milford, Del.) were silanized with 4% (all by mass, unless otherwise noted) 3-methacryloxypropyltrimethoxysilane and 2% n-propylamine. A resin of BisGMA (bisphenol glycidyl dimethacrylate) and TEGDMA (triethylene glycol dimethacrylate) at 1:1 mass ratio was rendered light-curable with 0.2% camphorquinone and 0.8% ethyl 4-N,N-dimethylaminobenzoate (referred to as the BisGMA-TEGDMA resin). This resin was filled with 30% NanoACP and 35% glass, following a previous study (Xu et al., 2011). For convenience, this composite is referred to as "NanoACP". Fabrication of QAS and Silver Nanocomposites The synthesis of bis(2-methacryloyloxy-ethyl) dimethyl-ammonium bromide is described recently (Antonucci et al., 2011). Since it is a quaternary ammonium dimethacrylate, it is referred to as QADM. Its synthesis was carried out using a modified Menschutkin reaction, where a tertiary amine group was reacted with an organo-halide. A benefit to this reaction was that the reaction products were generated at quantitative amounts and required no further purification (Antonucci et al., 2011). Briefly, 10 mmol of 2-(N,N-dimethylamino)ethyl methacrylate (DMAEMA, Sigma-Aldrich, St. Louis, Mo.) and 10 mmol of 2-bromoethyl methacrylate (BEMA, Monomer-Polymer and Dajec Labs, Trevose, Pa.) were combined with 3 g of ethanol in a 20 mL scintillation vial. A magnetic stir bar was added, and the vial was stirred at 60° C. for 24 h. The solvent was removed via evaporation, forming a clear, colorless and viscous liquid. The QADM thus obtained was then mixed with the photo-activated BisGMA-TEGDMA resin at a QADM mass fraction of 20%. This is referred to as the BisGMA-TEGDMA-QADM resin. A previous study showed that 20% QADM greatly reduced bacterial growth on the composite surface (Antonucci et al., 2011). The BisGMA-TEGDMA-QADM resin was then filled with 30% NACP and 35% barium boroaluminosilicate glass, and this composite is referred to as "NanoACP+QADM". Hence, the QADM mass fraction in the final composite was 20%×35%=7%.

Silver 2-ethylhexanoate powder (Strem Chemicals, New Buryport, Mass.) at 0.08 g was dissolved into 1 g of 2-(tert-butylamino) ethyl methacrylate (TBAEMA, Sigma) by gentle stirring, and then 1% of this solution was added to the resin. The mass fraction of the Ag salt over the total amount of resin was 0.08%, following a recent study (Cheng et al., 2011). TBAEMA improves the solubility by forming Ag—N coordination bonds with Ag ions, thereby facilitating the Ag salt to dissolve in the resin solution. TBAEMA was specifically selected since it contains reactive methacrylate groups and therefore can be chemically incorporated into the polymer network upon photopolymerization (Cheng et al., 2011).

To fabricate the "NACP+NanoAg" composite, the Ag-TBAEMA was mixed with the BisGMA-TEGDMA resin, and then 30% NACP and 35% glass were added to the resin. To fabricate the "NACP+QADM+NanoAg" composite, the Ag-TBAEMA was mixed with the BisGMA-TEGDMA-QADM resin. The NACP and glass filler levels were selected in preliminary studies to yield a cohesive paste that was readily mixed and not dry. The total filler level for NACP and glass was kept the same at 65% for all experimental composites. Each paste was placed into rectangular molds of (2×2×25) mm for mechanical testing, and disk molds of 9 mm in diameter and 2 mm in thickness for biofilm experiments. The specimens were photo-polymerized (Triad 2000, Dentsply, York, Pa.) for 1 min on each side.

Four nanocomposites were thus made: (1) NanoACP composite, (2) NanoACP+QADM composite, (3) NanoACP+NanoAg composite, and (4) NanoACP+QADM+NanoAg composite.

In addition, a commercial composite with glass nanoparticles of 40 nm to 200 nm and a low level of F release was tested (Heliomolar, Ivoclar, Ontario, Canada), and is referred to as "CompositeF". The fillers were silica and ytterbium-trifluoride with a filler level of 66.7%. Heliomolar is indicated for Class I and Class II restorations in the posterior region, Class III and Class IV anterior restorations, Class V restorations, and pit and fissure sealing. Another commercial composite, Renamel (Cosmedent, Chicago, Ill.), served as a non-releasing control (referred to as "CompositeNoF"). It consisted of nanofillers of 20 nm to 40 nm with 60% (by mass) fillers in a multifunctional methacrylate ester resin (Lee et al., 2005). Renamel is indicated for Class III, IV, and V restorations. The control specimens were also photo-cured in the same manner as described above.

Transmission Electron Microscopy (TEM)

TEM was performed to examine the silver nanoparticles in the resin. The mass fraction of the Ag salt was 0.08% in the resin, the same as that described above. Following a previous study (Cheng Y et al., 2011), a thin sheet of mica was partially split and the Ag-containing resin was placed in the gap. The resin-mica sandwich was pressed with an applied load of $2.7 \times 10^7$ N to form a thin sheet of resin in between the two mica layers (Cheng Y et al., 2011). The resin in the mica was photo-cured for 1 min on each side in the same manner as described above. The mica sheet was then split apart after 1 day using a scalpel to expose the polymerized film. An ultrathin layer of carbon was vacuum-evaporated onto the composite (Electron Microscopy Sciences, Hatfield, Pa.). The carbon-coated sample was then partial submerged in distilled water in order to float the thin film onto the water's surface. A copper grid was then used to retrieve the film. After drying, TEM was performed using a Tecnai T12 high resolution transmission electron microscope (FEI Company, Hillsboro, Oreg.) using an accelerating voltage of 120 kV. The TEM images were collected and the sizes of the silver particles were measured using AMT V600 image analysis software (Advanced Microscopy Techniques, Woburn, Mass.).

Flexural Testing

The composite bars were immersed in distilled water at 37° C. for 1 day. Specimens were then fractured in three-point flexure with a 10-mm span at a crosshead-speed of 1 mm/min on a computer-controlled Universal Testing Machine (5500R, MTS, Cary, N.C.). Flexural strength was calculated by: $S=3P_{max}L/(2bh^2)$, where P. is the fracture load, L is span, b is specimen width and h is thickness. Elastic modulus was calculated by: $E=(P/d)(L^3/[4bh^3])$, where load P divided by displacement d is the slope of the load-displacement curve in the linear elastic region.

S. mutans Inoculation and Live/Dead Assay

S. mutans was selected because it is a cariogenic bacterium and is the primary causative agent of dental caries (Loesche, 1986). S. mutans bacteria were obtained commercially (ATCC 700610, UA159, American Type Culture, Manassas, Va.). Their use was approved by the University of Maryland. The growth medium consisted of brain heart infusion (BHI) broth (BD, Franklin Lakes, N.J.) supplemented with 0.2% sucrose. Fifteen µL of stock bacteria was added into 15 mL of growth medium and incubated at 37° C. with 5% $CO_2$ for 16 h, during which the S. mutans were suspended in the BHI broth. The inoculation medium was formed by diluting this S. mutans culture by 10-fold in the growth medium (Cheng L et al., 2011).

Composite disks were sterilized in an ethylene oxide sterilizer (Anprolene AN 74i, Andersen, Haw River, N.C.). Each disk was placed in a well of a 24-well plate and inoculated with 1.5 mL of inoculation medium. The samples were incubated at 5% $CO_2$ and 37° C. for 1 d to form the initial biofilms on the disk, or 3 d to form mature biofilms. The growth medium was changed every 24 h, by transferring the disks to a new 24-well plate with fresh growth medium. After 1 d or 3 d, the biofilms on the disks were washed three times with PBS to remove loose bacteria, and then stained using the BacLight live/dead bacterial viability kit (Molecular Probes, Eugene, Oreg.). Live bacteria were stained with Syto 9 to produce green fluorescence, and bacteria with compromised membranes were stained with propidium iodide to produce red fluorescence. The stained disks were examined using an inverted epifluorescence microscope (Eclipse TE2000-S, Nikon, Melville, N.Y.). At each time period, three disks were evaluated for each material yielding 12 images for each condition.

MTT Metabolic Assay

The composite disks were placed in a 24-well plate, inoculated with 1.5 mL of the inoculation medium, and cultured for 1 d or 3 d. Each disk was then transferred to a new 24-well plate for the MTT (3-(4,5-Dimethylthiazol-2-yl)-2,5-diphenyltetrazolium bromide) assay. It is a colorimetric assay that measures the enzymatic reduction of MTT, a yellow tetrazole, to formazan. MTT assay for S. mutans biofilms was previously described (Kraigsley et al., 2011). Briefly, 1 mL of MTT dye (0.5 mg/mL MTT in PBS) was added to each well and incubated at 37° C. in 5% $CO_2$ for 1 h. During this process, metabolically active bacteria metabolized the MTT and reduced it to purple formazan inside the living cells. After 1 h, the disks were transferred to a new 24-well plate, 1 mL of dimethyl sulfoxide (DMSO) was added to solubilize the formazan crystals, and the plate was incubated for 20 min with gentle mixing at room temperature in the dark. After brief mixing via pipetting, 200 µL of the DMSO solution from each well was transferred to a 96-well plate, and the absorbance at 540 nm ($OD_{540}$) was measured via a microplate reader (SpectraMax M5, Molecular Devices, Sunnvale, Calif.). A higher absorbance indicates a higher formazan concentration, which in turn indicates more metabolic activity in the biofilm present on the composite disk.

Lactic Acid Production and Viable Cell Counts

Composite disks with 3-d biofilms were rinsed in cysteine peptone water (CPW) to remove loose bacteria. Each disk was placed in a new 24-well plate and 1.5 mL of buffered peptone water (BPW) supplemented with 0.2% sucrose was added. BPW medium was used so that the mature biofilm would remain stable during the 3-h culture for the acid production assay. BPW has a relatively high buffer capacity and the pH would not become significantly acidic, because a low pH would hinder bacterial acid production. Disks with biofilms were incubated at 5% $CO_2$ and 37° C. for 3 h to allow the biofilms to produce acid. After 3 h, the BPW solutions were stored for lactate analysis. Lactate concentrations in the BPW solutions were determined using an enzymatic (lactate dehydrogenase) method (van Loveren et al., 2000). The microplate reader was used to measure the absorbance at 340 nm (optical density $OD_{340}$) for the collected BPW solutions. Standard curves were prepared using a standard lactic acid (Supelco Analytical, Bellefonte, Pa.).

After the disks with biofilms were treated for lactic acid production, colony-forming unit (CFU) counts were used to quantify the total number of viable bacteria present on each composite disk. When biofilms are properly dispersed and diluted, each viable bacterium results in a single, countable colony on an agar plate. The disks were transferred into tubes with 2 mL CPW. The biofilms were harvested by sonication (3510R-MTH, Branson Ultrasonics, Danbury, Conn.) for 3 minutes, and then vortexing at maximum speed for 20 s using a vortex mixer (Fisher, Pittsburgh, Pa.). This removed and dispersed the biofilms from the disk. The bacterial suspensions were serially diluted, spread onto BHI agar plates, and incubated for 3 d at 5% $CO_2$ and 37° C. At 1 d and 3 d, the number of colonies that grew were counted and used, along with the dilution factor, to calculate total CFUs on each disk.

Statistical Analysis

One-way and two-way analyses of variance (ANOVA) were performed to detect the significant effects of the variables. Tukey's multiple comparison test was used to compare the data at a p-value of 0.05. Each standard deviation (sd) serves as the estimate for the standard uncertainty associated with a particular measurement.

Results

Figure 14:
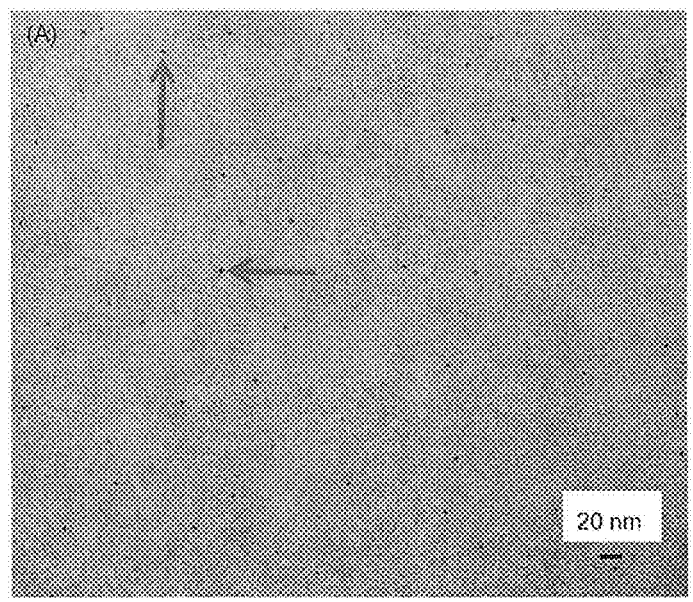
FIG. 14—Representative TEM micrographs of the size and dispersion of silver nanoparticles in the resin matrix: (A) lower and (B) high magnification. Silver 2-ethylhexanoate salt was dissolved in 2-(tert-butylamino) ethyl methacrylate and incorporated into a BisGMA-TEGDMA resin at a silver salt mass fraction of 0.08%. The silver nanoparticles were formed in the resin matrix by simultaneous reduction of the silver salt and photopolymerization of the dimethacrylates. The particle size was measured (mean±sd; n=20) to be (2.7±0.6) nm. Arrows indicate the silver nanoparticles, which were well dispersed in the resin with minimal appearance of nanoparticle aggregates.
Figure 14:
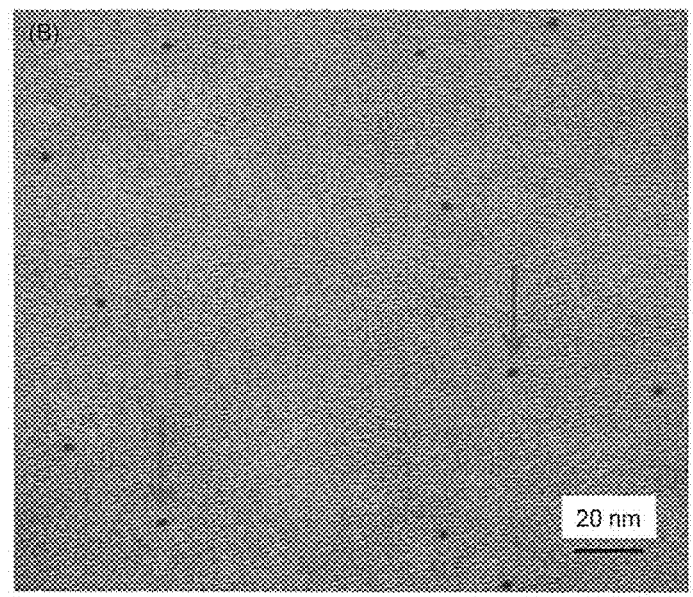

Typical TEM micrographs of the Ag nanoparticles in the resin are shown in FIG. 14: (A) Ag nanoparticles at a lower magnification, and (B) Ag nanoparticles at a high magnification. The Ag particle size was measured using an image analysis software to be (2.7±0.6) nm. The particles appeared to be well dispersed in the resin matrix, without noticeable clustered particles or significant agglomerates.

Figure 15:
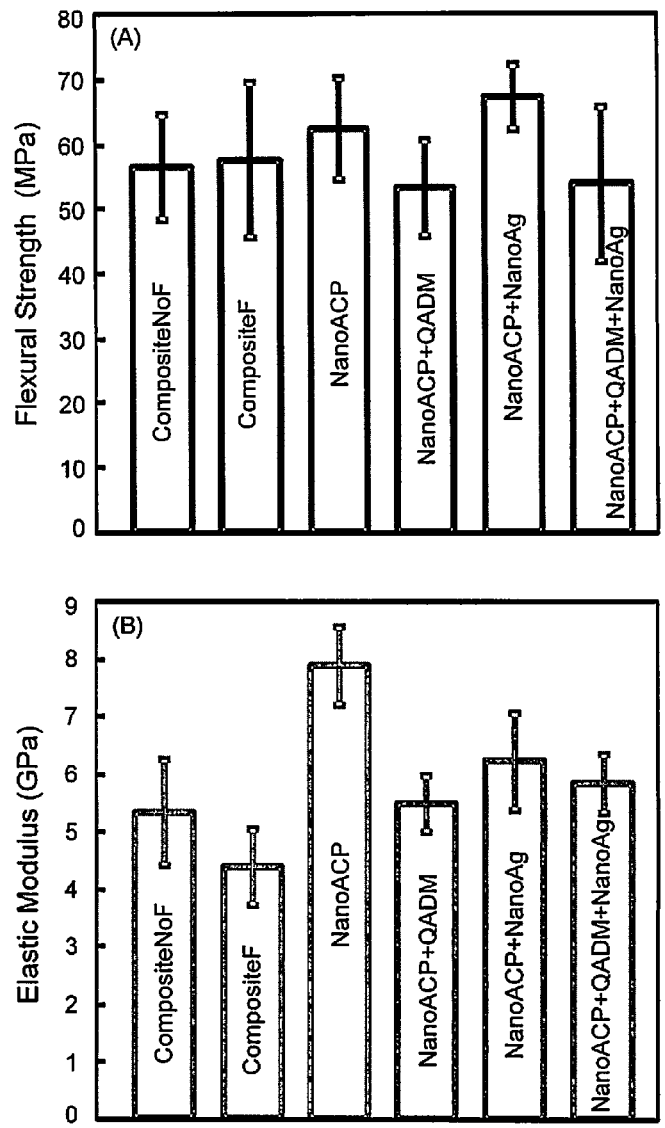
FIG. 15—Composite mechanical properties: (A) flexural strength, and (B) elastic modulus. Each value is the mean of six measurements with the error bar showing one standard deviation (mean±sd; n=6).

Mechanical properties are plotted in FIG. 15 for (A) flexural strength, and (B) elastic modulus, of the new nanocomposites along with the two commercial composites. NanoACP composite had a strength (mean±sd; n=6) of (62±8) MPa, not significantly different from the (57±12) MPa of CompositeF, and (56±9) MPa of CompositeNoF (p>0.1). Adding QADM, NanoAg, or QADM+NanoAg yielded strengths of (53±7) MPa, (67±6) MPa and (54±12) MPa, respectively. These composites had similar strengths (p>0.1). While the NanoACP had a significantly higher elastic modulus (p<0.05), all other composites had similar moduli (p>0.1).

Figure 16:
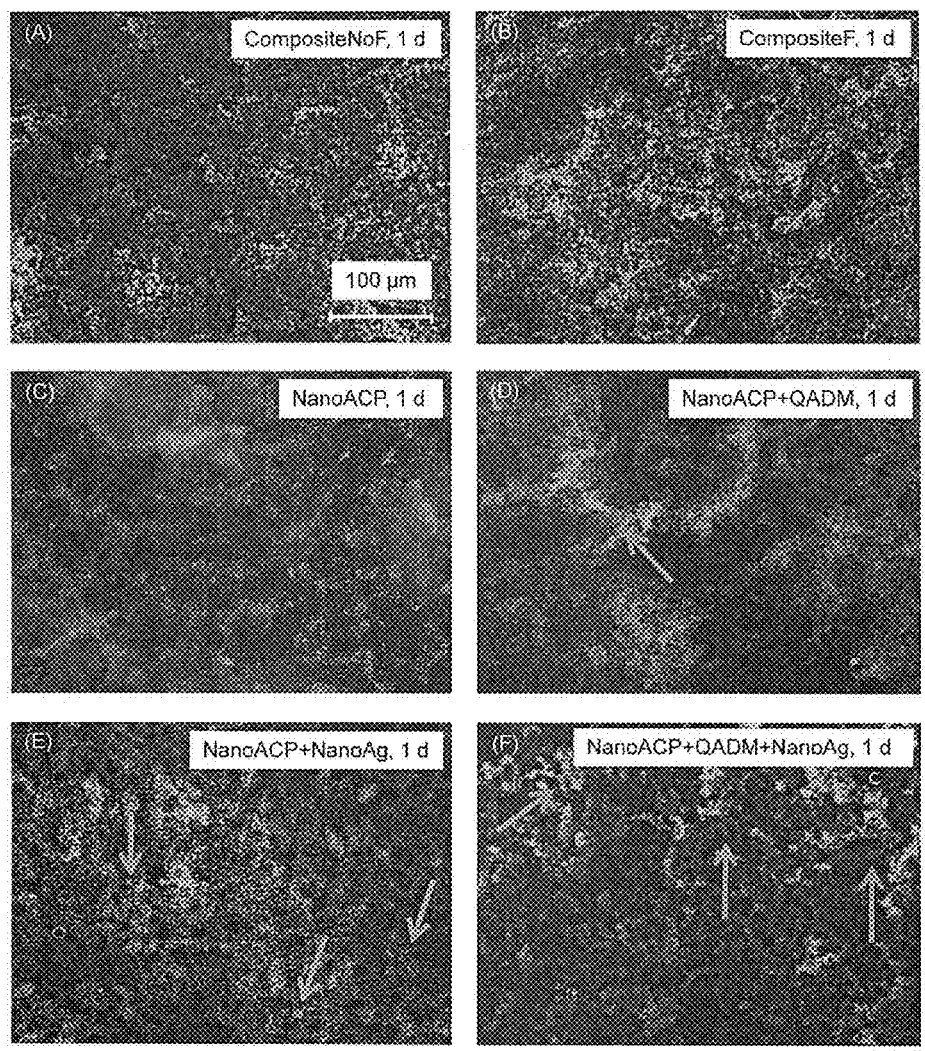
FIG. 16—Live/dead fluorescence images of *S. mutans* biofilms on composites at 1 d: (A) CompositeNoF, (B) CompositeF, (C) NanoACP, (D) NanoACP+QADM, (E) NanoACP+

FIG. 16 shows typical live/dead staining photos of biofilms on composites at 1 d. Live bacteria were stained green, and the compromised bacteria were stained red. When the live and dead bacteria were close to each other or on the top of each other, the green staining was mixed with the red, resulting in yellowish or orange colors. The biofilms on CompositeNoF, CompositeF, and NanoACP were predominantly viable, with relatively small amounts of dead cells. There was a slightly increase in the amount of dead cells on NanoACP+QADM, as indicated by the arrow in (D). There were noticeably less green staining, and more red/orange staining, in the biofilms on NanoACP+NanoAg (arrows in E). The numbers of dead bacteria, indicated by the red/orange staining, further increased in the biofilms on NanoACP+QADM+NanoAg (arrows in F).

The 3-d live/dead biofilm images are shown in FIG. 17. On CompositeNoF, CompositeF, and NanoACP, S. mutans had formed mature biofilms in which the staining was mostly green, indicating that the bacteria were primarily alive. NanoACP+QADM had slightly more dead bacteria (arrow in D). The amount of compromised bacteria significantly increased in (E) on NanoACP+NanoAg. Visual examination revealed that NanoACP+QADM+NanoAg had the most red/orange staining, indicating the most amounts of compromised bacteria.

FIG. 18 plots the biofilm metabolic activity measured via the MTT assay at (A) 1 d, and (B) 3 d. At both 1 d and 3 d, CompositeNoF had the highest MTT absorbance, indicating the highest metabolic activity in the biofilms adherent on the composite disks. The incorporation of QADM and NanoAg into the NanoACP composite significantly decreased the metabolic activity of the S. mutans biofilms (p<0.05). Furthermore, incorporating QADM and NanoAg together into the same composite resulted in the lowest metabolic activity (p<0.05).

FIG. 19 plots the CFU counts. At 1 d, the CFU counts were 27 million per disk for CompositeNoF and 21 million for NanoACP. The CFU counts were greatly reduced to 12.5 million on NanoACP+QADM composite, 3.2 million on NanoACP+NanoAg composite, and 1.4 million on NanoACP+QADM+NanoAg composite (p<0.05). The ranking of CFU at 1 d is maintained at 3 d, with the NanoACP+QADM+NanoAg composite having the least CFU counts, which were an order of magnitude less than that of CompositeNoF.

FIG. 20 plots the lactic acid production by the biofilms on the composites. The biofilms on CompositeNoF produced the most acid, closely followed by that of CompositeF and NanoACP. The incorporation of either QADM or NanoAg into the NanoACP composite significantly decreased the acid production (p<0.05). When both QADM and NanoAg were incorporated, the composite resulted in the lowest acid production by the biofilms (p<0.05). The biofilm acid production on NanoACP+QADM+NanoAg composite was nearly ⅓ that on CompositeNoF.

Discussion

In the present study, silver and quaternary ammonium monomer were incorporated into ACP nanocomposite for the first time. The NanoACP+QADM+NanoAg composite greatly reduced the S. mutans biofilm growth, metabolic activity, CFU counts, and lactic acid production, compared to two commercial composites. Meanwhile, NanoACP+QADM+NanoAg possessed mechanical properties similar to the commercial composites. In the oral environment, bacteria colonize on the tooth-restoration surface to form a biofilm, which is a heterogeneous structure consisting of clusters of various types of bacteria embedded in an extracellular matrix (Stoodley et al., 2008). Cariogenic bacteria such as S. mutans and lactobacilli in the plaque metabolize carbohydrates to acids, which causes demineralization to the tooth structure and the tooth-restoration margins beneath the biofilm. Therefore, the new nanocomposite with a great reduction in S. mutans biofilm growth and acid production is promising to combat recurrent caries.

The present study showed that biofilms on the composite with no F release had the highest metabolic activity, CFU counts, and acid production. This is consistent with previous studies that showed that, in general, resin composites had no antimicrobial capability and accumulated more biofilms and plaque in vitro and in vivo compared to other restorative materials (Svanberg et al., 1990; Zalkind et al., 1998; Beyth et al., 2007). The present study showed that the composite with F release (CompositeF) reduced the biofilm growth, yielding lower CFU counts and less acid production, compared to CompositeNoF. This is also consistent with previous studies, which showed that F ions reduced the acid production of the biofilms (Deng et al., 2005). The reason for the reduction in acid production by bacteria was suggested to be the F ions inhibiting the metabolic pathways such as the fermentation pathway of the bacteria for the lactic acid production (Stoodley et al., 2008). In addition, the present study showed that the NanoACP composite also had a reduction in biofilm growth and acid production, similar to that of CompositeF. It is possible that the alkalinity of the NanoACP fillers may reduce the bacteria growth (Moreau et al., 2011). It should be noted that another merit of the NanoACP composite is its release of calcium (Ca) and phosphate ($PO_4$) ions (Xu et al., 2011). The amount of release was similar to those in previous studies that effectively remineralized tooth lesions in vitro (Dickens et al., 2003; Langhorst et al., 2009). The NanoACP was combined with antibacterial agents QADM and silver nanoparticles in the present study for the first time. The purpose was to combine the best of both worlds: The remineralization capability of NanoACP, and the antibacterial activity of QADM and NanoAg.

Previous studies either used QAS or Ag in the composites. So far there have been no reports on the use of QAS and Ag nanoparticles together in the same composite. In the present study, visual examination of the live/dead images indicated that the composite with QADM and NanoAg had the least amount of live bacteria (green staining) and the most amount of compromised bacteria (yellow/orange staining). Quantitative measurements showed that the incorporation of both QADM and NanoAg together in the same composite significantly lowered the CFU counts, metabolic activity, and lactic acid production, compared to either QADM or Ag alone. The NanoACP+QADM+NanoAg composite had the lowest CFU, metabolic activity, and acid production of the biofilms. Therefore, this study showed that it is beneficial to use double agents (QADM+NanoAg) than a single agent in the composite. Among the three antibacterial nanocomposites, NanoACP+QADM+NanoAg is advantageous because it has the strongest antibacterial effects, while being mechanically as strong as the other composites.

Besides antibacterial properties, the composite needs to possess sufficient load-bearing capability for tooth cavity restorations. The major challenges facing composite restorations are secondary caries and bulk fracture (Sakaguchi, 2005; Sarrett, 2005). In the present study, adding QADM and Ag to the NanoACP composite did not significantly decrease the strength. The strengths of NanoACP+QADM, NanoACP+NanoAg, and NanoACP+QADM+NanoAg were similar to those of the two commercial composites. The elastic moduli of the antibacterial nanocomposites also matched those of the two commercial composites. This is likely because the nanocomposites contained not only ACP nanoparticles, but also 35% of barium boroaluminosilicate glass particles for reinforcement. According to the manufacturers, CompositeF (Heliomolar) is indicated for Class I and II posterior restorations and Class III and IV anterior restorations, and CompositeNoF (Renamel) is indicated for Class III, IV, and V restorations. Therefore, the antibacterial NanoACP+ QADM, NanoACP+NanoAg, and NanoACP+QADM+ NanoAg with similar strength and elastic modulus may also be suitable for these applications. These new nanocomposites have two added benefits: the release of Ca and $PO_4$ ions for remineralization (Xu et al., 2011), and the antibacterial ability shown in this study. Further efforts are needed to optimize the design and processing of the nanocomposite, and to investigate systematically the physical, antibiofilm and anti-caries properties.

All documents, books, manuals, papers, patents, published patent applications, guides, abstracts and other reference materials cited herein are incorporated by reference in their entirety. While the foregoing specification teaches the principles of the present invention, with examples provided for the purpose of illustration, it will be appreciated by one skilled in the art from reading this disclosure that various changes in form and detail can be made without departing from the true scope of the invention.

CITED DOCUMENTS

Antonucci J M, Fowler B O, Zeiger D N, Lin N J, Lin-Gibson S. Synthesis and characterization of dimethacrylates containing quaternary ammonium functionalities for dental applications. Dent Mater (in review, 2011).

Bayne S C, Thompson J Y, Swift Jr. E J, Stamatiades P, Wilkerson M (1998). A characterization of first-generation flowable composites. *J Am Dent Assoc* 129:567-577.

Beyth N, Yudovin-Farber I, Bahir R, Domb A J, Weiss E I. Antibacterial activity of dental composites containing quaternary ammonium polyethylenimine nanoparticles against *Streptococcus mutans*. Biomaterials 2006; 27:3995-4002.

Beyth N, Domb A J, Weiss E. An in vitro quantitative antibacterial analysis of amalgam and composite resins. J Dent 2007; 35:201-206.

Burne R A (1998). Oral Streptococci . . . Products of their environment. *J Dent Res* 77:445-452.

Carlén A, Nikdel K, Wennerberg A, Holmberg K, Olsson J. Surface characteristics and in vitro biofilm formation on glass ionomer and composite resin (2001). *Biomaterials* 22:481-487.

Cenci M S, Pereira-Cenci T, Cury J A, ten Cate J M. Relationship between gap size and dentine secondary caries formation assessed in a microcosm biofilm model (2009). *Caries Res* 43:97-102.

Cheng L, Weir M D, Xu H H K, Kraigsley A M, Lin N, Lin-Gibson S, Zhou X. Antibacterial and physical properties of calcium-phosphate and calcium-fluoride nanocomposites with chlorhexidine. J Biomed Mater Res B (2011, in review).

Cheng Y J, Zeiger D N, Howarter J A, Zhang X, Lin N J, Antonucci J M, Lin-Gibson S. In situ formation of silver nanoparticles in photocrosslinking polymers. J Biomed Mater Res B 2011; 97:124-131.

Chow L C, Markovic M, Takagi S. Calcium phosphate cements. In: Cements research progress. Struble L J, editor. Westerville, Ohio: American Ceramic Society, 1999. p 2152-238.

Chow L C, Sun L, Hockey B (2004). Properties of nanostructured hydroxyapatite prepared by a spray drying technique. *J Res NIST* 109:543-551.

Damm C, Munsted H, Rosch A. Long-term antimicrobial polyamide 6/silver nanocomposites. J Mater Sci 2007; 42:6067-6073.

Dawes C (2003). What is the critical pH and why does a tooth dissolve in acid? *J Can Dent Assoc* 69:722-724.

Deng D M, ten Cate J M (2004). Demineralization of dentin by *Streptococcus mutans* biofilms grown in the constant depth film fermentor. *Caries Res* 38:54-61.

Deng D M, van Loveren C, ten Cate J M (2005). Cariespreventive agents induce remineralization of dentin in a biofilm model. *Caries Res* 39-216-223.

Dickens S H, Flaim G M, Takagi S (2003). Mechanical properties and biochemical activity of remineralizing resin-based Ca—$Pa_r$ cements. *Dent Mater* 19:558-566.

Deligeorgi V, Mjor I A, Wilson N H (2001). An overview of reasons for the placement and replacement of restorations. *Prim Dent Care* 8:5-11.

Drummond J L, Bapna M S (2003). Static and cyclic loading of fiber-reinforced dental resin. *Dent Mater* 19:226-231.

Drummond J L (2008). Degradation, fatigue, and failure of resin dental composite materials. *J Dent Res* 87:710-719.

Fan C, Chu L, Rawls H R, Norling B K, Cardenas H L, Whang K. Development of an antimicrobial resin—A pilot study. *Dent Mater* 2011; 27:322-328.

Featherstone J D B (2000). The science and practice of caries prevention. *J Am Dent Assoc* 131:887-899.

Featherstone J D B (2004). The continuum of dental caries—Evidence for a dynamic disease process. *J Dent Res* 83: C39-C42.

Ferracane J L (1995). Current trends in dental composites. *Crit Rev Oral Biol Med* 6:302-318.

Frost P M (2002). An audit on the placement and replacement of restorations in a general dental practice. *Prim Dent Care* 9:31-36.

Hefferren J J, Koehler H M (1981). Foods, nutrition and dental health. Pathotox Publishers, Park Forest South, Ill., p. 138.

Hostacka A, Ciznar I, Stefkovicova M (2010). Temperature and pH affect the production of bacterial biofilm. Folia Microbiol 55:75-78.

Imazato S, Torii M, Tsuchitani Y, McCabe J F, Russell R R B (1994). Incorporation of bacterial inhibitor into resin composite. *J Dent Res* 73; 1437-1443.

Imazato S (2003). Review: Antibacterial properties of resin composites and dentin bonding systems. *Dent Mater* 19:449-457.

Imazato S. Bioactive restorative materials with antibacterial effects: new dimension of innovation in restorative dentistry. *Dent Mater J* 2009; 28:11-19.

Jokstad A, Bayne S, Blunck U, Tyas M, Wilson N (2001). Quality of dental restorations. FDI Commision Projects 2-95. *International Dent J* 51:117-158.

Kraigsley A M, Lin-Gibson S, Lin N J. Effects of polymer degree of conversion on oral biofilm metabolic activity and biomass. Biomaterials 2011 (in review).

Kramer N, Garcia-Godoy F, Reinelt C, Frankenberger R (2006). Clinical performance of posterior compomer restorations over 4 years. *Am J Dent* 19:61-66.

Langhorst S E, O'Donnell J N R, Skrtic D. In vitro remineralization of enamel by polymeric amorphous calcium phosphate composite: Quantitative microradiographic study. Dent Mater 2009; 25:884-891.

Lee S B, Koepsel R R, Morley S W, Matyjaszewski K, Sun Y, Russell A J. Permanent, nonleaching antibacterial surface. 1. Synthesis by atom transfer radical polymerization. Biomacromolecules 2004; 5:877-882.

Lee B S, Lin Y\V, Chia J S, Hsieh T T, Chen Lin C P, Lan W H (2006). Bactericidal effects of diode laser on *streptococcus inutans* after irradiation through different thickness of dentin, *Lasers in Surg Med* 38:62-69.

Lee Y, Lu H, Oguri M, Powers J M. Changes in gloss after simulated generalized wear of composite resins. J Prosthet Dent 2005; 94:370-376.

Li F, Chen J, Chai Z, Zhang L, Xiao Y, Fang M, Ma S. Effects of a dental adhesive incorporating antibacterial monomer on the growth, adherence and membrane integrity of *Streptococcus mutans*. J Dent 2009; 37:289-296.

Li P, Li J, Wu C, Wu Q, Li J. Synergistic antibacterial effects of f3-lactam antibiotic combined with silver nanoparticles. Nanotechnology 2005; 16:1912-1917.

Lim B S, Ferracane J L, Sakaguchi R L, Condon J R (2002). Reduction of polymerization contraction stress for dental composites by two-step light-activation. *Dent Mater* 18:436-444.

Loesche W J (1986). Role of *Streptococcus mutans* in human dental decay. Microbiological Reviews 50:353-380.

Lu H, Stansbury J W, and C. N. Bowman C N (2005). Impact of curing protocol on conversion and shrinkage stress. *J Dent Res* 84:822-826.

Mjor I A, Moorhead J E, Dahl J E (2000). Reasons for replacement of restorations in permanent teeth in general dental practice. *International Dent J*50:361-366.

Moreau J L, Sun L, Chow L C, Xu HHK. Mechanical and acid neutralizing properties and inhibition of bacterial growth of amorphous calcium phosphate dental nanocomposite. J Biomed Mater Res Part B (2011, accepted for publication).

Namba N, Yoshida Y, Nagaoka N, Takashima S, Matsuura-Yoshimoto K, Maeda H, Van Meerbeek B, Suzuki K, Takashida S. Antibacterial effect of bactericide immobilized in resin matrix. Dent Mater 2009; 25:424-430.

Percival S L, Bowler P G, Russell D. Bacterial resistance to silver in wound care. J Hospital Infection 2005; 60:1-7.

Rai M, Yada A, Gade A. Silver nanoparticles as a new generation of antimicrobials. Biotechnol Adv 2009; 27:76-83.

Ruddell D E, M. M. Maloney M M, Thompson J Y (2002). Effect of novel filler particles on the mechanical and wear properties of dental composites. *Dent Mater* 18:72-80.

Sakaguchi R L (2005). Review of the current status and challenges for dental posterior restorative composites: clinical, chemistry, and physical behavior considerations. *Dent Mater* 21:3-6.

Sarrett D C (2005). Clinical challenges and the relevance of materials testing for posterior composite restorations. *Dent Mater* 21:9-20.

Skrtic D, Antonucci J M, Eanes E D (1996). Improved properties of amorphous calcium phosphate fillers in remineralizing resin composites. *Dent Mater* 12:295-301.

Slenters T V, Hauser-Gerspach I, Daniels A U, Fromm K M. Silver coordination compounds as light-stable, nano-structured and anti-bacterial coatings for dental implant and restorative materials. J Mater Chem 2008; 18:5359-5362.

Stoodley P, Wefel J, Gieseke A, deBeer D, von Ohle C (2008). Biofilm plaque and hydrodynamic effects on mass transfer, fluoride delivery and caries. *J Am Dent Assoc* 139:1182-1190.

Svanberg M, Mjor I A, rstavik D (1990). Mutans streptococci in plaque from margins of amalgam, composite, and glass-ionomer restorations. *J Dent Res* 69; 861-864.

Takahashi Y, Imazato S, Russell R R B, Noiri Y, Ebisu S (2004). Influence of resin monomers on growth of oral streptococci. *J Dent Res* 83:302-306.

Tanagawa M, Yoshida K, Matsumoto S, Yamada T, Atsuta M. Inhibitory effect of antibacterial resin composite against *Streptococcus mutans*. Caries Res 1999; 33:366-371.

Tezvergil-Mutluay A, Agee K A, Uchiyama T, Imazato S, Mutluay M M, Cadenaro M, Breschi L, Nishitani Y, Tay F R, Pashley D H. The inhibitory effects of quaternary ammonium methacrylates on soluble and matrix-bound MMPs. J Dent Res 2011; 90:535-540.

Thylstrup A, Fejerskov O. Textbook of cariology. Copenhagen, Denmark, Munksgaard, 1986, p. 145-146.

Totiam P, Gonzalez-Cabezas C, Fontana M R, Zero D T (2007). A new in vitro model to study the relationship of gap size and secondary caries. *Caries Res* 41:467-473.

van Dijken J W V, Sjostrom S (1991). The effect of glass ionomer cement and composite resin filling on marginal gingival. *J Clin Periodontol* 18:200-203.

van Houte J (1994). Role of micro-organisms in caries etiology. *J Dent Res* 73:672-681.

van Loveren C, Buijs J F, ten Cate J M. The effect of triclosan toothpaste on enamel demineralization in a bacterial demineralization model. J Antimicrob Chemo 2000; 45:153-158.

Watts D C, Marouf A S, Al-Hindi A M (2003). Photo-polymerization shrinkage-stress kinetics in resin-composites: methods development. *Dent Mater* 19:1-11.

Xie D, Weng Y, Guo X, Zhao J, Gregory R L, Zheng C. Preparation and evaluation of a novel glass-ionomer cement with antibacterial functions. Dent Mater 2011; 27:487-496.

Xu H H K, Simon C G (2005). Fast setting calcium phosphate-chitosan scaffold: mechanical properties and biocompatibility. *Biomaterials* 26:1337-1348.

Xu H H K, Sun L, Weir M D, Antonucci J M, Takagi S, Chow L C (2006). Nano dicalcium phosphate anhydrous-whisker composites with high strength and Ca and $PO_4$ release. *J Dent Res* 85:722-727.

Xu H H K, Weir M D, Sun L, Takagi S, Chow L C (2007a). Effect of calcium phosphate nanoparticles on Ca—$Pa_t$ composites. *J Dent Res* 86:378-383.

Xu H H K, Weir M D, Sun L (2007b). Dental nanocomposites with Ca—$Pa_4$ release: Effects of reinforcement, dicalcium phosphate particle size and silanization. *Dent Mater* 23:1482-1491.

Xu H H K, Moreau J L, Sun L, Chow L C (2008). Strength and fluoride release characteristics of a calcium fluoride based dental nanocomposite. *Biomaterials* 29:4261-4267.

Xu H H K, Weir M D, Sun L (2009). Calcium and phosphate ion releasing composite: Effect of pH on release and mechanical properties. *Dent Mater* 25:535-542.

Xu H H K, Weir M D, Sun L, Moreau J L, Takagi S, Chow L C, Antonucci J M. Strong nanocomposites with Ca, $PO_4$ and F release for caries inhibition. *J Dent Res* 2010; 89:19-28.

Xu H H K, Moreau J L, Sun L, Chow L C. Nanocomposite containing amorphous calcium phosphate nanoparticles for caries inhibition. *Dent Mater* 2011 (accepted).

Xu X, Ling L, Wang R, Burgess J O (2006). Formation and characterization of a novel fluoride-releasing dental composite. *Dent Mater* 22:1014-1023.\

Yamamoto K, Ohashi S, Aono M, Kokubo T, Yamada I, Yamauchi J. Antibacterial activity of silver ions implanted in $SiO_2$ filler on oral streptococci. Dent Mater 1996; 12:227-229.

Zalkind M M, Keisar O, Ever-Hadani P, Grinberg R, Sela M N. Accumulation of *Streptococcus mutans* on light-cured composites and amalgam: An in vitro study. J Esthet Dent 1998; 10:187-190.

Zero D T (1995). In situ caries models. *Adv Dent Res* 9:214-230.

What is claimed is:

1. A dental composite comprising (i) nanoparticles of amorphous calcium phosphate (NACP), (ii) a filler, and (iii) a resin comprising anti-bacterial agents, wherein the NACP particles range in size from about 10 nm to about 500 nm, and where the NACP comprises about 20% to about 40% of the mass of the composite, and wherein the anti-bacterial agents are silver-containing nanoparticles (NanoAgs) and bis(2-methacryloyloxy-ethyl) dimethyl-ammonium bromide (QADM).

2. The dental composite of claim 1, wherein the filler is selected from the group consisting of a glass filler, a ceramic filler, and a polymer-based filler.

3. The dental composite of claim 2, wherein the filler is a glass filler selected from the group consisting of barium boroaluminosilicate, strontium-alumino-fluoro-silicate glass, silicon dioxide, fluoroaluminosilicate glass, a ytterbium tri-fluoride filler, and a fiber glass filler.

4. The dental composite of claim 3, wherein the filler is barium boroaluminosilicate.

5. The dental composite of claim 2, wherein the filler is a ceramic filler selected from the group consisting of a porcelain filler, a quartz filler, and a zirconia filler.

6. The dental composite of claim 1, wherein the resin is one or more resins selected from the group consisting of bis-GMA (bisphenol glycidyl methacrylate), TEGDMA (triethylene glycol dimethacrylate), HEMA (2-hydroxyethyl methacrylate), UDMA (urethane dimethacrylate), PMGDM (pyromellitic acid glycerol dimethacrylate), ethoxylated bisphenol A dimethacrylate (EBPADMA), methacryloyloxy-ethyl phthalate (MEP), methacrylate-modified polyalkenoic acid, a hydrophobic monomer, a hydrophilic monomer, a poly acid-modified polymer, a light-cured polymer, a self-cured polymer, a duel cured polymer, and a heat-cured polymer.

7. The dental composite of claim 6, wherein the resin is a 1:1 mass ratio of bis-GMA and TEGDMA.

8. The dental composite of claim 6, wherein the resin further comprises one or more additional anti-bacterial agents selected from the group consisting of a quaternary ammonium salt (QAS), chlorhexidine particles, $TiO_2$ particles and ZnO particles.

9. The dental composite of claim 8, wherein the QAS is selected from the group consisting of methacryloyloxydodecylpyridinium bromide, methacryloxylethyl benzyl dimethyl ammonium chloride, methacryloxylethyl m-chloro benzyl dimethyl ammonium chloride, methacryloxylethyl cetyl dimethyl ammonium chloride, cetylpyridinium chloride, and methacryloxylethyl cetyl ammonium chloride, a QAS chloride, a QAS bromide, a QAS monomethacrylate, a QAS dimethacrylate, and pre-fabricated QAS particles.

10. The dental composite of claim 6, wherein the resin further comprises a QAS present in an amount of between about 5% and about 70% of the mass fraction of the resin.

11. The dental composite of claim 6, wherein the resin further comprises NanoAgs present in an amount of between about 0.01% and about 20% of the mass fraction of the resin.

12. The dental composite of claim 1, wherein the NACP particles range in size from about 50 nm to about 200 nm.

13. A dental composite comprising (i) about 30% by mass NACP, (ii) about 35% by mass glass filler, and (iii) about 35% by mass resin, wherein the NACP particles range in size from about 50 nm to about 200 nm, and wherein the resin comprises silver-containing nanoparticles (NanoAgs) and bis(2-methacryloyloxy-ethyl) dimethyl-ammonium bromide (QADM) as anti-bacterial agents.

14. The dental composite of claim 13, wherein the glass filler is barium boroaluminosilicate.

15. The dental composite of claim 13, wherein the resin is a 1:1 mass ratio of bis-GMA and TEGDMA.

16. The dental composite of claim 13, wherein the QADM is present in an amount of between about 15% and about 55% of the mass fraction of the resin.

17. The dental composite of claim 16, wherein the QADM is present in an amount of about 20% of the mass fraction of the resin.

18. The dental composite of claim 13, wherein the NanoAgs are present in an amount of between about 0.01% and about 10% of the mass fraction of the resin.

19. The dental composite of claim 18, wherein the silver-containing nanoparticles (NanoAgs) are present in an amount of about 0.08% of the mass fraction of the resin.

20. A dental composite comprising (i) about 30% by mass nanoparticles of amorphous calcium phosphate (NACP) (ii) about 35% by mass barium boroaluminosilicate, and (iii) about 35% by mass resin, wherein the NACP particles range in size from about 50 nm to about 200 nm, wherein the resin is a 1:1 mass ratio of bis-GMA (bisphenol glycidyl methacrylate) and TEGDMA (triethylene glycol dimethacrylate), and wherein the resin comprises silver—containing nanoparticles (NanoAgs in an amount of about 0.08% of the mass fraction of the resin and bis(2-methacryloyloxy-ethyl) dimethyl-ammonium bromide (QADM in an amount of about 20% of the mass fraction of the resin.

* * * * *